United States Patent [19]
Roever et al.

[11] Patent Number: 6,157,730
[45] Date of Patent: Dec. 5, 2000

[54] VISUAL INSPECTION SYSTEM FOR LEATHER HIDE

[76] Inventors: Detlef E. Roever, 10 Berry Street, Cronulla, Sydney, NSW 2230; Wei Wen, 2 Ethel Street, Randwick, Sydney, NSW 2033; Hartmut Kaebernick, 10/11-15 Goodchap Road, Chatswood, Sydney, NSW 2067; Khoi Hoang, 14 Maitland Avenue, Kingsford, Sydney, NSW 2032, all of Australia

[21] Appl. No.: 09/429,208

[22] Filed: Oct. 28, 1999

Related U.S. Application Data

[63] Continuation of application No. PCT/AU97/00067, Feb. 10, 1997, and a continuation of application No. 09/131,629, Aug. 10, 1998.

[30] Foreign Application Priority Data

Feb. 9, 1996 [AU] Australia .................................. PN8007

[51] Int. Cl.⁷ ............................. G06K 9/00; G01N 21/89
[52] U.S. Cl. .......................................... 382/110; 382/111
[58] Field of Search .................................... 382/108, 110, 382/111; 348/88, 89, 128, 131; 356/430, 431, 238.1, 237.2; 250/559.04, 559.05, 559.07, 559.45

[56] References Cited

U.S. PATENT DOCUMENTS

| | | | |
|---|---|---|---|
| 4,671,663 | 6/1987 | Sick | 356/430 |
| 4,914,308 | 4/1990 | Hochgraf | 250/572 |
| 5,185,822 | 2/1993 | Miura | 382/65 |
| 5,570,188 | 10/1996 | Nevel et al. | 356/385 |

FOREIGN PATENT DOCUMENTS

| | | | |
|---|---|---|---|
| 85629/91 | 4/1992 | Australia | G01N 21/88 |
| 662774 | 9/1995 | Australia | G01N 21/64 |
| 0226430 | 6/1987 | European Pat. Off. | G01N 21/88 |
| 0352797 | 1/1990 | European Pat. Off. | G01N 21/88 |
| 0 742 431 | 11/1996 | European Pat. Off. | G01N 21/89 |
| 4216469 | 11/1993 | Germany | G01N 21/88 |
| 4-70563 | 3/1992 | Japan | G01N 33/44 |
| 6-207909 | 7/1994 | Japan | G01N 21/88 |

OTHER PUBLICATIONS

Limas-Serafin, "Natural Images' Segmentation for Patterns' Recognition Using Edges' Pyramids and its Application to the Leather' Defects," *IEEE Proc. of IECON '93 Int. Conf. on Industrial Electronics, Control and Instrumentation*, Nov. 15-19, 1993, vol. 3, pp. 1357-1360.

*Primary Examiner*—Andrew W. Johns
*Attorney, Agent, or Firm*—Rader, Fishman, Grauer & McGarry, an office of Rader, Fishman & Grauer PLLC

[57] ABSTRACT

A visual inspection system particularly designed for imaging relatively non-rigid materials. In order to identify defects and the position of defects and the position of defects on the material. The arrangement is particularly designed for handling leather hide. Defects in leather hide are presently identified by manual inspection. The present invention provides a visual inspection system for non-rigid materials comprising a mounting means for mounting a sample of the material, tensioning means for tensioning at least an area of the sample, an imaging means (3) for obtaining an image of the area of the sample under tension and processing means for processing the image to provide information on any defects which may exist.

21 Claims, 20 Drawing Sheets

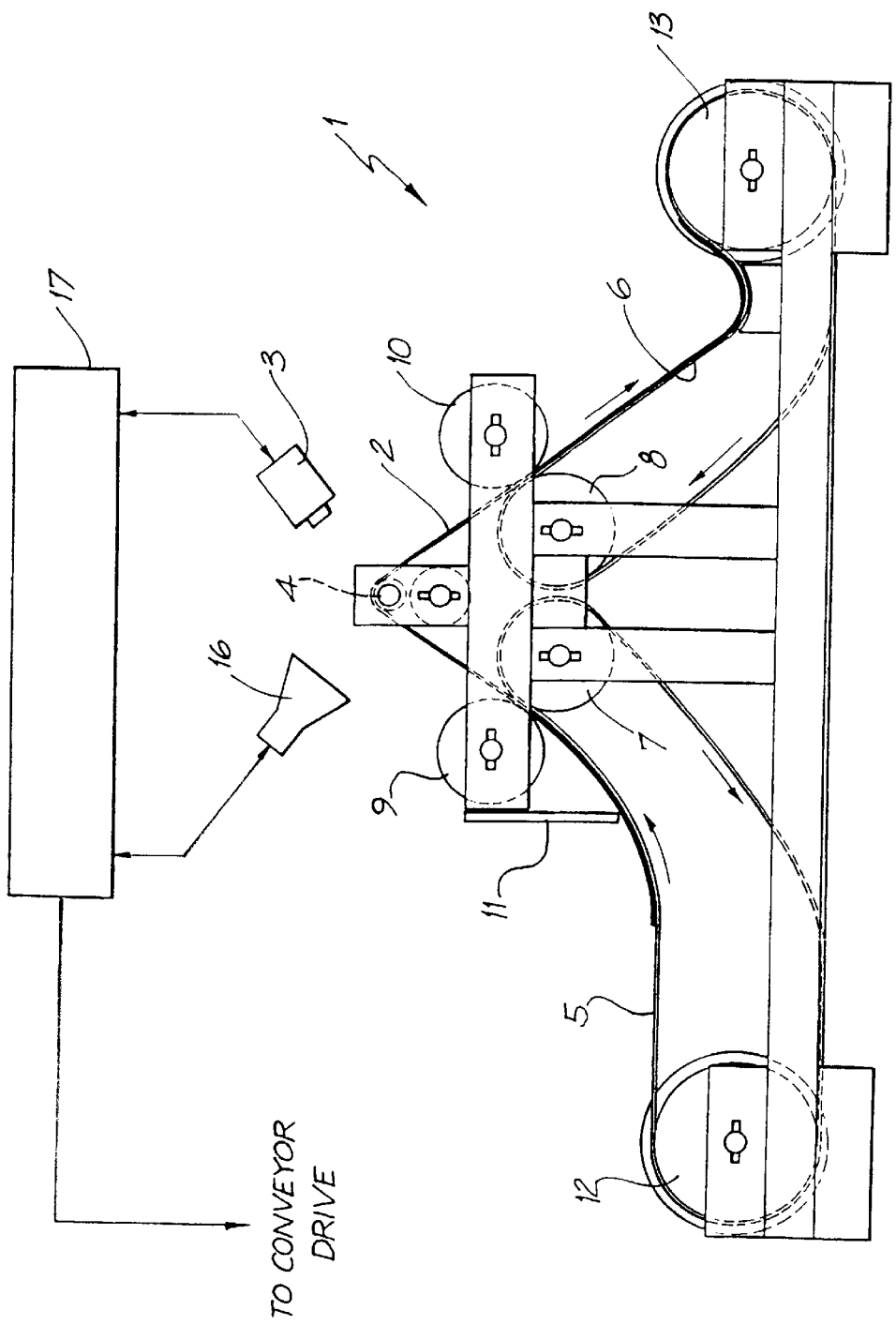

| | | DEPTH (mm) | | | |
|---|---|---|---|---|---|
| | | 0 | 0.1 | 0.5 | 2 |
| S | 2 | N | (A) | D | D |
| I | 5 | (A) | B | D | D |
| Z | 10 | (A) | (B) | D | D |
| E | 25 | (A) | (B) | D | D |
| | 50 | (A) | (B) | D | D |
| (mm²) | 100 | d | D | D | D |
| | 250 | d | D | D | D |

( ) = SEALED

VISUAL INSPECTION SYSTEM FOR LEATHER HIDE

This application is a continuation of International Application No. PCT/AU97/00067, filed Feb. 10, 1997, and claims the benefit of the Australian Patent Application No. PN8007, filed Feb. 9, 1996, and a con of Ser. No. 09/131,629 Aug. 10, 1998.

BACKGROUND OF THE INVENTION

1. Field of the Invention

The present invention relates generally to a visual inspection system and, particularly, but not exclusively, to a visual inspection system for inspecting leather hides.

2. Description of Related Art

The effect of damage caused to the hide of an animal during its lifetime is a major problem for the tanning industry. Such damage may result in defects existing in the processed leather hide, in the form of scars, abrasions and the like. The nature and quantity of defects existing in any particular hide will effect its application in the manufacture of leather goods. Areas of hide containing defects may be considered unusable, or useful only for particular purposes.

It is necessary to visually inspect each hide to determine the nature and distribution of defects, in order to "rank", the hide in terms of quality and sale price. Further, in the initial stages of manufacture of leather goods it is also necessary to inspect a hide to determine the location of non-defective areas which can be used in manufacture. For example, in the manufacture of shoes, shoe components of different sizes and shapes are "nested" within the hide geometry and cut manually using dies and a swing beam press. In the nesting and cutting operations, the operator must avoid defects.

Visual inspection of the hide, both for ranking and nesting/cutting, is presently carried out manually by skilled operators.

In the ranking process, an assessment is made of the degree to which the existent damage will effect the cutting yield, and the hide is priced accordingly. This assessment is of necessity subjective, based on the operators skill and experience. A subjective analysis can lead to non-uniformity in ranking between respective operators, and has resulted in disputes between tanners, pricing the hide, and leather goods manufacturers, purchasing the hide. In Australia, rates of return of hides from leather goods manufacturers to tanners as a result of disputes over ranking of hides run as high as 15% and result in disruption in production schedules and costs to both the manufacturer and tanner.

In the nesting/cutting process, a skilled operator attempts to achieve both optimum layout of patterns for components of leather goods and avoid defects unsuited for manufacture of the particular leather goods. This is an almost impossible task. Wastage of 34%. on average of raw material is common, in Australia. Further, under current manual cutting methods, the variation in yield between operators is in the order of 10%, depending upon the skill of the particular operator.

An automated visual inspection process, which may provide a more objective approach, may save operator costs and provide for more efficient utilization of material, is therefore desirable. Development of an automated system presents a number of problems, however.

Leather hide and like materials are non-rigid or "floppy". Any imaging device would have difficulty obtaining an accurate image of defects and distinguishing from shadows cast by raised or lowered areas of the hide caused by the "floppiness". Further, certain types of defects in animal hide may be invisible unless the hide is deformed before viewing. Such defects include scars which have become "sealed" because they healed in the animals lifetime. Present examination for sealed scars involves the operator stretching the hide over his finger to make the sealed scars more visible. This presents a significant hide manipulation problem for any proposed automatic process.

Difficulties also lie in processing an image from an imaging device to distinguish between defective and non-defective areas of a hide.

SUMMARY OF THE INVENTION

The present invention provides a visual inspection system for non-rigid materials, comprising a mounting means for mounting a sample of the material, tensioning means for tensioning at least an area of the sample, an imaging means for obtaining an image of the area of the sample under tension and processing means for processing the image to provide information on any defects which may exist.

The system is preferably arranged for inspection of leather hide, although it is possible that the invention could be applied for inspection of other materials, particularly, but not exclusively, non-rigid or "floppy" materials.

Tension is applied to the material so as to reveal any "hidden defects". Where the material is leather hide, enough tension should be applied to make any sealed scars sufficiently visible to enable detection by the imaging device. Preferably, the hide is tensioned over a former. In one embodiment the former is a relatively small diameter roller. In an alternative embodiment the former has a substantially flat surface.

Tension is preferably applied to the hide in such a direction as to promote visibility of the majority of hidden defects existing in the hide. To facilitate this, the hide is preferably fed over the former during the imaging process in a direction perpendicular to the direction of the backbone of the animal in its lifetime. It is considered the majority of scars likely to have been obtained by the animal in its lifetime will run in substantially the same direction as the backbone (i.e. in the direction the animal walked when alive).

In a preferred embodiment, tension is applied in at least two directions, one direction being substantially at right angles to the other direction. This maximizes the opportunity for opening and revealing all defects in the hide.

In a preferred embodiment, this dual tensioning is facilitated by a former which comprises a plurality of substantially flat areas for supporting areas of the hide sample to be imaged, separated by depressions. The hide is tensioned in a first direction perpendicular to the extending direction of the former over the substantially flat portions, and is tensioned in a second direction, which is in the same direction as the extending direction of the former, by pressing portions of the hide into the depressed portions, applying tension to the portions of the hide extending over the flat portions.

A light source is preferably provided to illuminate the area of the hide being imaged. The relative positions of the light source, hide and imaging device are preferably such that the imaging device perceives defect areas as having lower and higher "grey level" (i.e. being darker or lighter) than non-defect areas. This may be because defect areas are cast into shadow and/or cause bright reflecting edges because of the relative positions of the light source camera and hide. The light source preferably provides a -strip of light focused onto the area of the hide being imaged and the imaging device is preferably a charge coupled device having a single line of pixels focused on the area illuminated by the strip. The entire hide is preferably passed over the former through the imaging area, so that its entire area is scanned line by line.

On a typical open scar, the edges will appear brighter than the surrounding surface, while the center of the open scar will be darker due to shadow. Sealed scars are visible because of their discoloration.

The intensity of the light source is preferably variable, so it may be adjusted to provide the best results for different colored hides. It has been found that, generally, the darker the hide, the higher intensity required for the light. Further, the higher the speed of the hide being passed over the former as it is being imaged, i.e. the higher the scanning speed of the imaging area, the higher the intensity required for the light source. Although variable intensities are preferably provided by the light source, at any one intensity the light distribution over the width of the scar should preferably be as uniform as possible. Variations in uniformity of the light source for any one image will increase the difficulty in processing the image to detect defects. Light sources may include a fiber optic array or a mirror tube.

The entire image detected by the camera is preferably not stored in memory and subsequently processed. This would take too much time. Instead, the picture is preferably analyzed on-line in real time as it is received, preferably to give a contour map showing the boundary areas of any defects together with associated information as to the character of the defects, and perimeter size of the hide. This "extracted information" is stored in memory.

In one embodiment, in order to determine that a defect exists, a statistical analysis of grey levels received for each pixel by the imaging device is preferably applied. The median of grey levels is considered to represent non-defective leather. A point on the median statistical curve sufficiently below or above the median (i.e. sufficiently darker or lighter) is defined as defected leather, i.e. anything below or above these points is considered to be a defect. The number of pixels below or above this grey level which are adjacent to each other gives an indication of the extent of the area of the defect. Further, the lower or higher the grey level the greater the depth or height of the defect, i.e. the darker the shadow or brighter the reflection cast by the light source onto the image area. A normal distribution is preferably used for the statistical curve. Calibration runs with different types of leather are preferably carried out in order to assist in setting the grey level limits as to what is and what is not a defect for that particular type and color of leather. The leather may therefore be classified according to type/color and different statistical analyses may be applied to different types of leather.

Quantitative definitions of leather defects are preferably stored in memory and the processing means compares information determined for each defect with the stored definition to classify the particular defect. Definition is preferably in terms of area size and depth of the defects.

In a preferred embodiment, after a hide has been processed the results are stored in memory as a map indicating size and location of the defects on the hide as a contour, together with information relating to the nature of the defect in relation to its area size and depth as classified by comparison with the stored quantitative definitions, and information on the total area and perimeter of the hide. A number of maps may be stored for each hide, e.g. giving different maps showing different classes of defects. The map or maps may be stored on recordable media, which may be supplied to the leather product manufacturer with the hide, so that the manufacturer is provided with a complete set of defect data to assist in subsequent processing.

Further, the processing means preferably applies an assessment technique to "rank" each leather hide. The assessment technique comprises scanning a template with known size across the stored map to identify cuttable areas of the leather which will be useful in leather product manufacture. For example, for in the shoe industry, the "quarter" concept is preferably used. A 5×12 cm mask is scanned across the stored map. 5×12 cm of undefected leather is the smallest amount of undetected leather useful in shoe manufacture. The template is first scanned vertically across the entire area of the leather sample (i.e. in a series of adjacent vertical columns), and then diagonally at 45° angles upwardly across the leather and downwardly across the leather (so that the two diagonals intersect each other at 90°), again scanning the entire surface in each direction. Information obtained from the scans is processed to give a value for total cuttable area for each hide and total defect area. This information can be used to objectively rank and price the particular leather hide. The processing means may apply a similar ranking process automatically, by "scanning" the stored extracted image.

The present invention further provides a method of visually inspecting materials, comprising mounting a sample of the material, applying tension to at least an area of the material, obtaining an image of the area of material from an imaging device and processing the image to provide information on any defects which may exist in the material.

BRIEF DESCRIPTION OF THE DRAWINGS

Features and advantages of the present invention will become apparent from the following description of embodiments thereof, by way of example only, with reference to the accompanying drawings, in which:

FIG. 1A is a schematic side view of a visual inspection system in accordance with a first embodiment of the present invention;

DETAILED DESCRIPTION

Figure 1B:
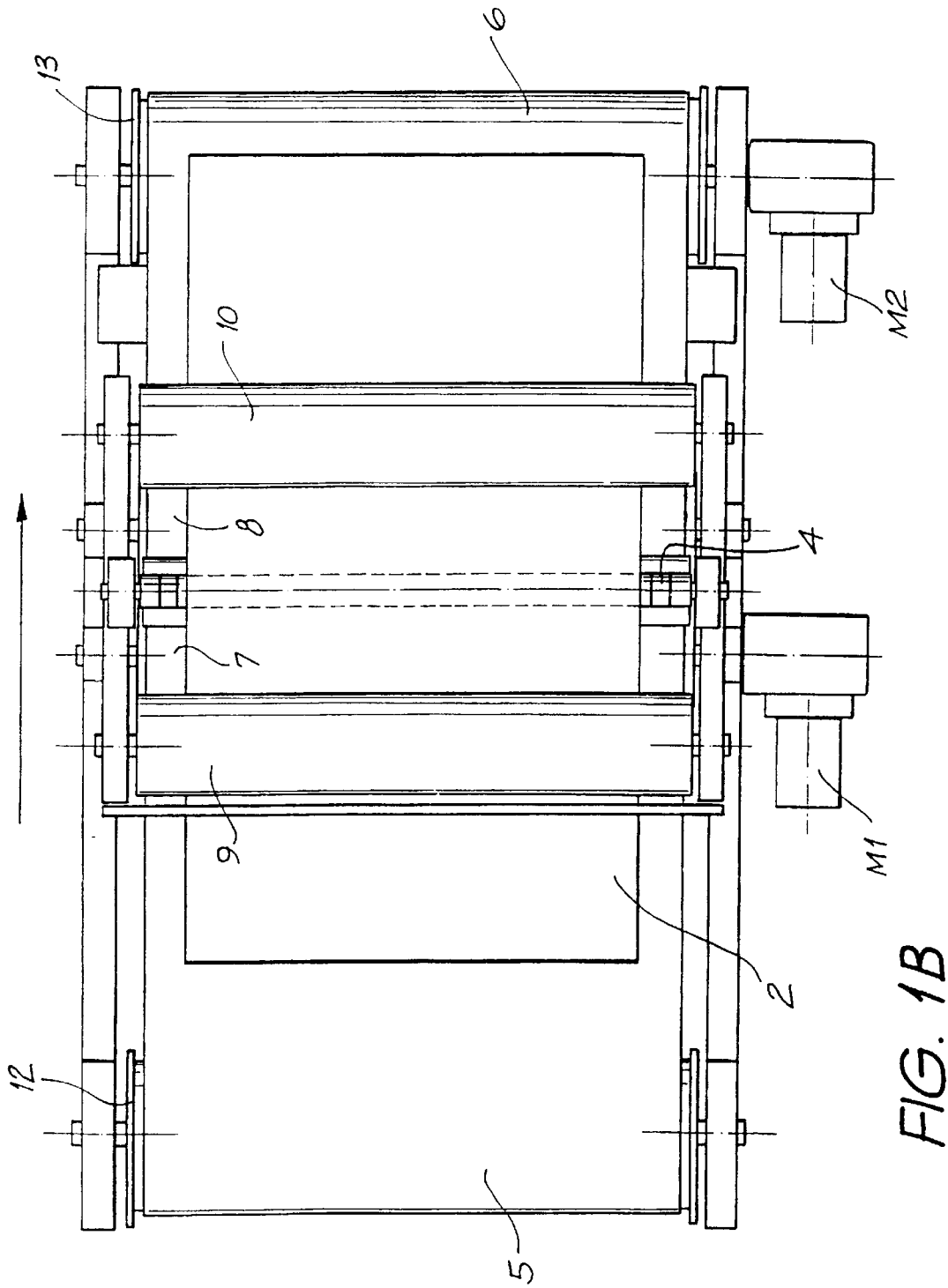
FIG. 1B is a plan view of the embodiment of FIG. 1A.

Reference numeral 1 generally designates a handling means 1 for mounting and handling a sample of leather hide 2 (or other non-rigid material) so that it can be imaged by CCD line scanner 3. Handling means 1 comprises a former, in this embodiment being a 12 mm diameter roller 4 over which the hide 2 is tensioned (12 mm has been found to be optimum for this handling means arrangement to enable applied tension to increase detectability of any hidden defects in a hide, without over-stretching the hide other diameters may still be useful, however). The leather sample 2 is supported by a pair of conveyor belts 5 and 6 running in directions as indicated by the arrows on the diagram of FIG. 1. The pair of conveyor belts 5 and 6 operate to transport the hide 2 from left to right as shown in the drawings, over the roller 4. The sample hide 2 is unsupported by the conveyors 5, 6 as it passes over roller 4, as indicated in FIG. 1. Conveyor 6 is arranged to run slightly faster than conveyor 5 in order to apply tension to the leather sample 2 as it passes over roller 4. The conveyors are driven by torque controlled motors $M_1$, $M_2$ (FIG. 1B).

The tension applied should be sufficient to allow the camera 3 to detect any hidden defects, such as sealed scars, in the leather. The value of the tension applied will depend upon the thickness, type of leather and size of hide. Calibration should be made with different types and thicknesses of leather to assess the optimum tensions to be applied for each type/thickness. Tensions will generally be in the order of 100–500N.

The handling means further comprises guide rollers 9 and 10, opposing rollers 7 and 8, respectively; a safety guide 11; a feed roller 12 for feeding leather samples onto conveyors 5 and 6, and a take up roller 13 for taking up processed leather sample. Handling means 1 is of sufficient dimension to process all leather hide sizes. In conventional tanneries, the guide roller should be in the order of one meter long in order to deal with leather hides of up to one meter in width.

Figure 2:
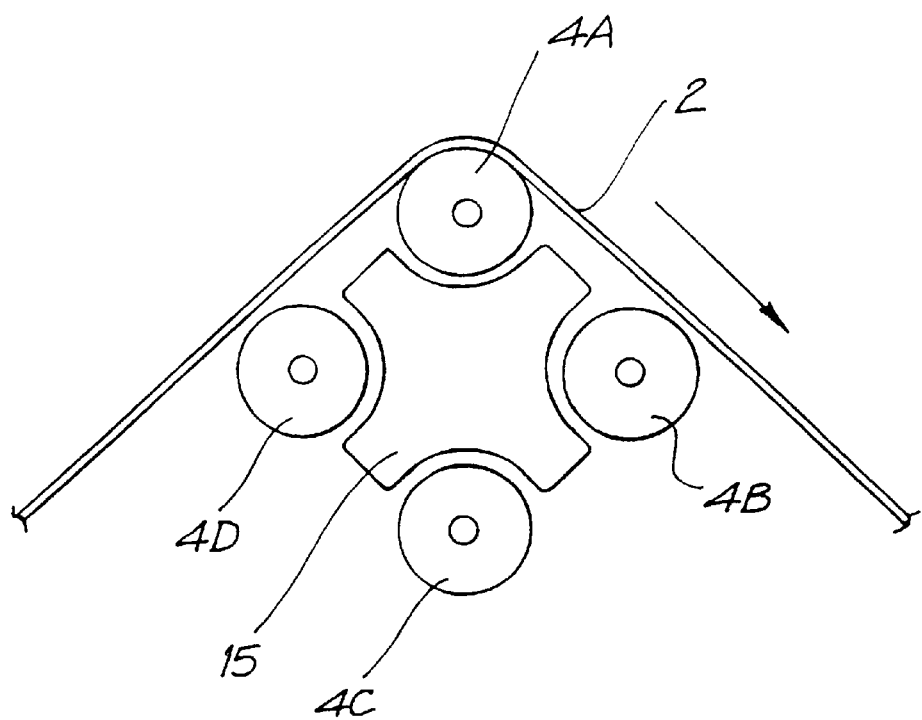
FIG. 2 is a detail of a modification to the system of FIG. 1.

The color of the former roller 4 should provide sufficient contrast with the color of the particular hide sample to enable the system to be able to detect and identify the hide perimeter. To enable the system to be used with hides of different color, a variation to the mounting arrangement, as shown in FIG. 2, is employed. Four former rollers 4A through 4D, are mounted on a centrally extending spindle 15. The spindle 15 can be rotated to change the position of the respective rollers 4A through 4D. Only one roller at any one time will be used as the roller to mount the leather sample. Each roller is a different color. The arrangement replaces the single roller 4 in FIG. 1, and facilitates inspection of hides of various colors.

A light source 16 is provided mounted on the opposite side of the roller 4 to the camera 3. The light source is set at an angle of 40° to the horizontal plane, and the camera is set at angle of 45° on the other side of the roller 4. Alternatively the light source may be set at 45° and the camera at 40°. It is preferred that there should be an angle of inclination between the light source and camera of 85–95° and that either the light source or camera should be offset at an angle of 5° more than the other. The light source uses an acrylic lens system to provide a strip of light focused on the leather sample being tensioned over the roller 4. The light source may comprise a fiber optic array or mirror tube. The camera has a single line of charge coupled devices for receiving light reflected from the leather sample 2. With this arrangement, it has been found that defects in the leather appear darker or lighter because the strip light source 16 casts a shadow in the defect area or causes an area of greater reflection. The defect area is therefore darker or lighter, or a mixture of both, than "background", background being undetected leather. Intensity of the light source 16 is controllable. It has been found that for darker leather samples, a higher intensity is required to achieve the best results. Further, if the scanning speed is increased (i.e. the speed of the leather being passed over the roller 4) it is also required to increase the intensity of the light source 16. Optimum intensity of the light source for different colored samples of leather may be established by calibration runs with different types/colors of leather.

The width of the imaging area may be from 0.1 mm upwards. In this embodiment the light strip is 5 mm in width. The length of the line is preferably in the order of 1,000 mm, although this can be varied to deal with requirements for different width of hide. In order to provide an imaging device capable of imaging a line of 1,000 mm width, it may be necessary to use a number of adjacently mounted CCD devices 3. In the present embodiment, pixel size is preferably 0.4 $mm^2$, and the camera/cameras are set up at an appropriate distance from the former roller 4 to provide this pixel size.

The camera 3 scans the leather a line at a time as it is passed over the roller 4. The image received by the camera 3 is transmitted to the processing means 17, where it is analyzed.

Rather than storing the entire image for subsequent processing, the image is analyzed in real time to extract relevant information and the relevant information is subsequently stored. This enables leather samples to be processed in reasonable time periods, in the order of 15 seconds per sample, for example.

The information required includes the following:

1. The location and extent of any defects.
2. The nature of the defects.
3. The extent of the perimeter of the sample hide.

Utilizing this information, the processing means constructs a "map" of the leather sample illustrating the defects in contour. Each defect is classified in accordance with a quantitative definition of leather defects stored in the processing means 17, the quantitative definition being on the basis of depth and area of the defects. A contour outline of the perimeter is also included in the map.

The camera 3 provides a "raw image" displaying a variation in grey level (i.e. variation in shade) across the image. The processing means 17 is arranged to make a determination as to which grey levels of the image indicate the existence of a defect. In this embodiment, a statistical analysis of the grey levels is applied.

Because of the relative orientations of the light source 16, sample 2 and camera 3, defects in the leather appear as shadows which are darker or areas which are lighter, or both, than the undefected leather. Areas containing defects will therefore be darker or lighter, or both, than areas having no defects. In analyzing the image, it must be determined at what level of darkness or lightness a defect should be defined.

The "background of a sample', i.e. the undefected leather background, is expected to be substantially homogenous i.e., there should only be small variation in the grey levels exhibited. Unfortunately, large variations do occur because of a non-random effect of the light source. In order to cope with this problem, each image is divided into small square areas of equal size, or "cells", in the preferred embodiment, each cell comprises $10^4$ pixels. It was found that each small area or cell could be regarded as approximately homogenous with respect to the effect of the operating conditions. This approach can be considered analogous to noise reduction through blocking in statistical experimental design.

The processing means is arranged to analyze each cell of the image separately and then build up the image cell by cell to provide a map containing the relevant information.

Figures 3, 4:
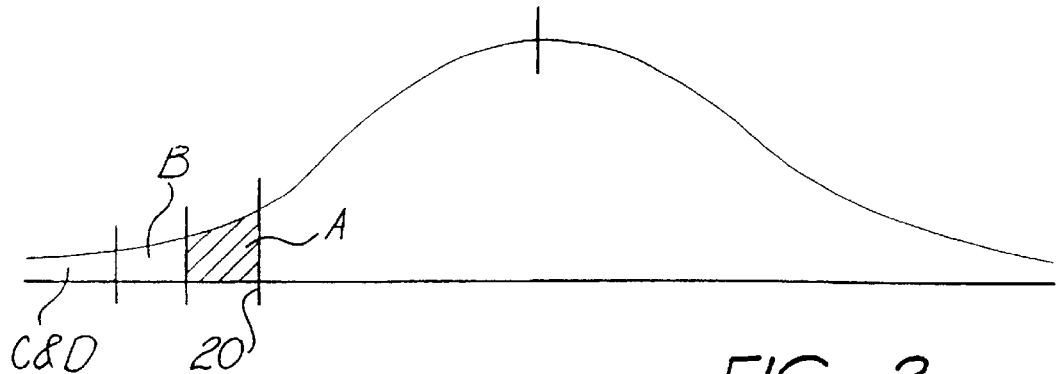
FIG. 3 is a diagram of a statistical distribution, used in the processing method applied in this embodiment.
FIG. 4 is a table giving an example of quantitative definition of leather defects, as applied in the processing means of this embodiment.

The median grey level of each cell is defined as the "background". Using a normal distribution, levels of the extreme of the distribution are defined by the processing means 17 as defects. In this embodiment, all the defects will be at the low, or//and high ends of the normal distribution, i.e. at low or high grey levels. FIG. 3 shows a normal distribution based around the median level of grey level. The left hand side of the curve contains grey levels which are darker than the right hand side. All pixels having a grey level below threshold 0.20 on the normal distribution curve are considered to belong to a defect. The threshold is selected by pre-calibrating the system for various different types and colors of leather and using standard statistical techniques. Different thresholds are provided to define different degrees of defect. An A defect is the least serious defect, progressing further down the curve, B defects and then C and D defects are also defined. C and D defects are the most serious defects. A similar calibration is provided for the extreme right hand side of the normal distribution, for defect areas which appear at higher grey levels because of higher reflectivity.

Using this type of statistical analysis, the processing means is able to build up, cell by cell, a map of the sample illustrating the location and extent of defects in contour. It is also able to classify the defects according to seriousness.

The grey level of the dark area is an indication of its depth (for open scars), because the light source casts a shadow in the area of the defect. The darker the shadow, it is assumed the greater the depth of the defect. A quantitative definition of defects can therefore be made, on the basis of depth and extent of area. FIG. 4 gives an example of a table showing the quantitative definition which has been established for this particular system. N indicates no defect. A, B and D indicate defects of increasing seriousness. Depth can be correlated with darkness of the pixels, using the normal distribution as discussed above. The defects are then further classified depending upon the area of extent of the particular defect.

Brackets around a defect classification indicate that it is a sealed defect.

It will be appreciated that other classifications may be employed to define defects, in alternative embodiments. It will obviously be advantageous for the industry to decide upon an objective classification of defects for uniform application of the system in accordance with the present invention.

The processing means 17 may produce a series of maps, as illustrated in FIG. 5.

Figure 5B:
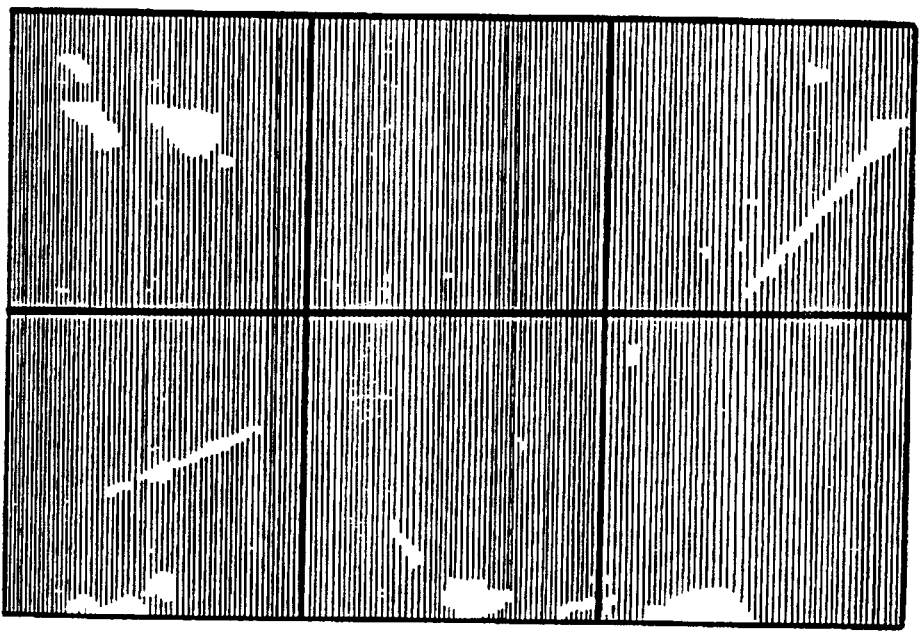
FIGS. 5A to G are example representations of raw and processed images of leather hide.
Figure 5A:
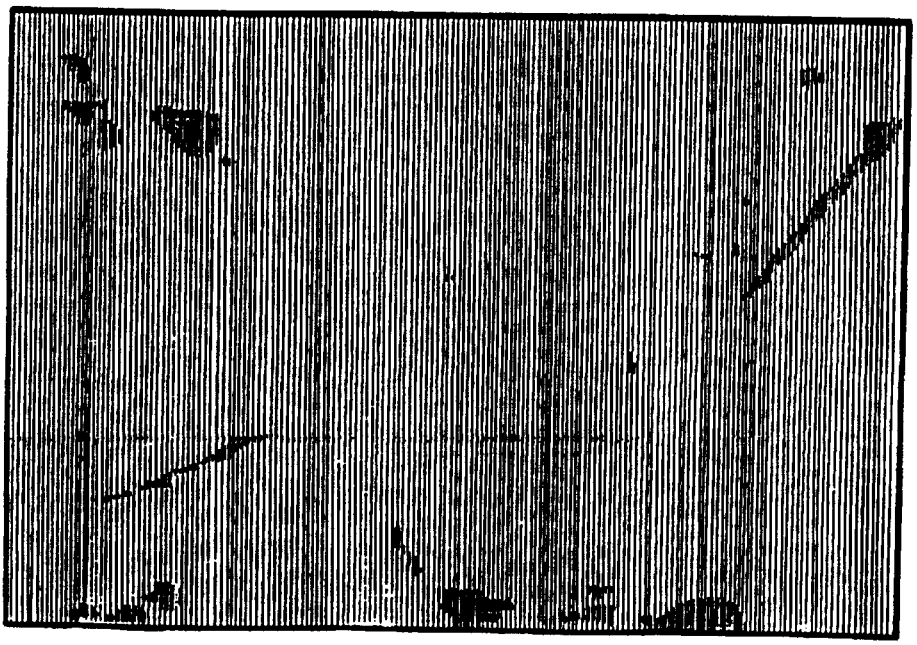

FIG. 5A shows the raw image as detected by the CCD camera 3. This is not stored. Instead, it is processed cell by cell, employing the processing technique discussed above.

FIG. 5B shows the raw image after feature extraction. Defects show up as white areas. Again, this image is not stored.

Figure 5D:
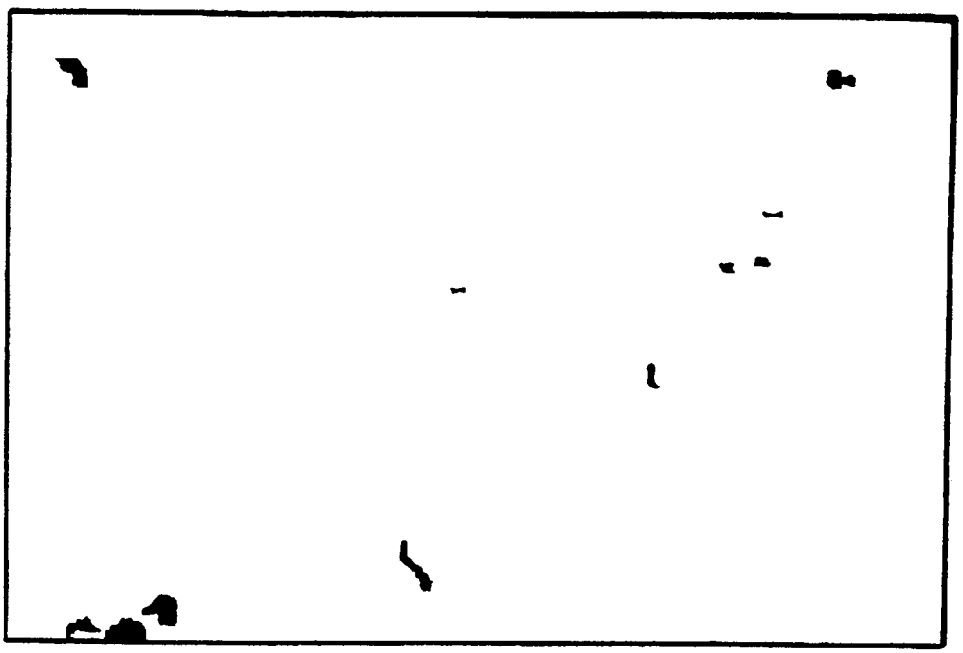
Figure 5C:

FIG. 5C shows a map of all defects extracted from the raw image. This image can be stored in memory.

Figure 5F:
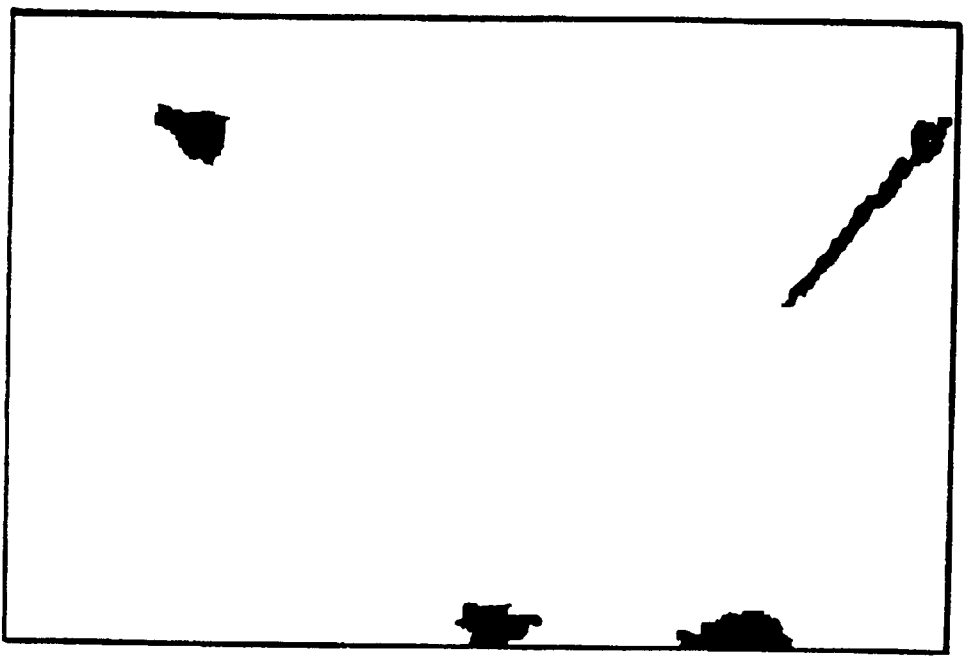
Figure 5E:
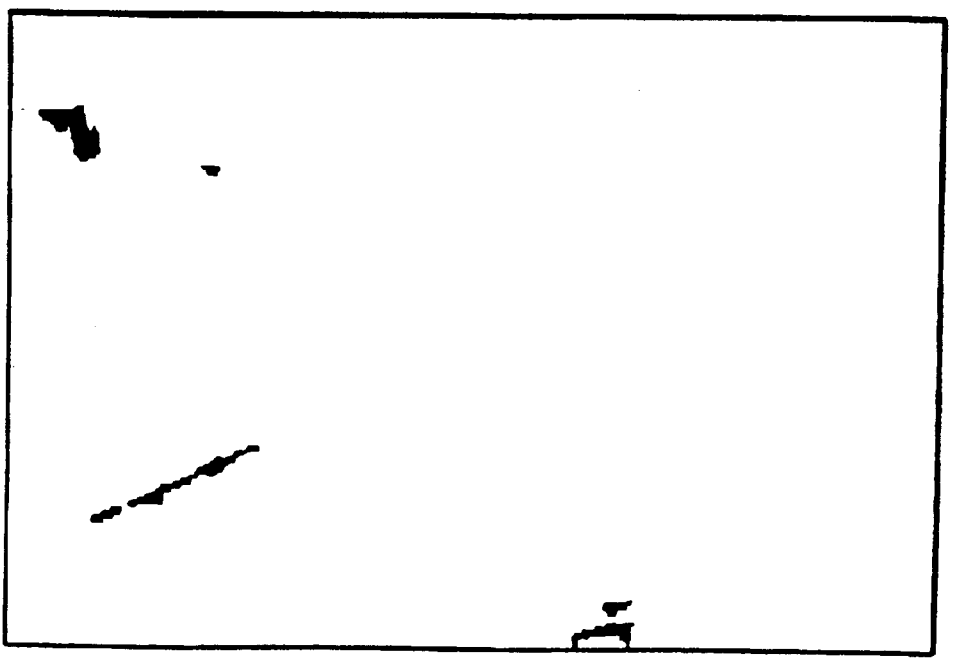

FIGS. 5D through 5F show B, C and D defects, respectively.

Figure 5G:

FIG. 5G is a contour map of all the defects.

Defects are first classified and maps provided of their location and extent. This information can be recorded on disk and provided to a leather goods manufacturer for use in processing the particular leather hide.

Further analysis of the stored maps is carried out by the processing means 17 in order to provide information useful for ranking the leather.

Figure 6:
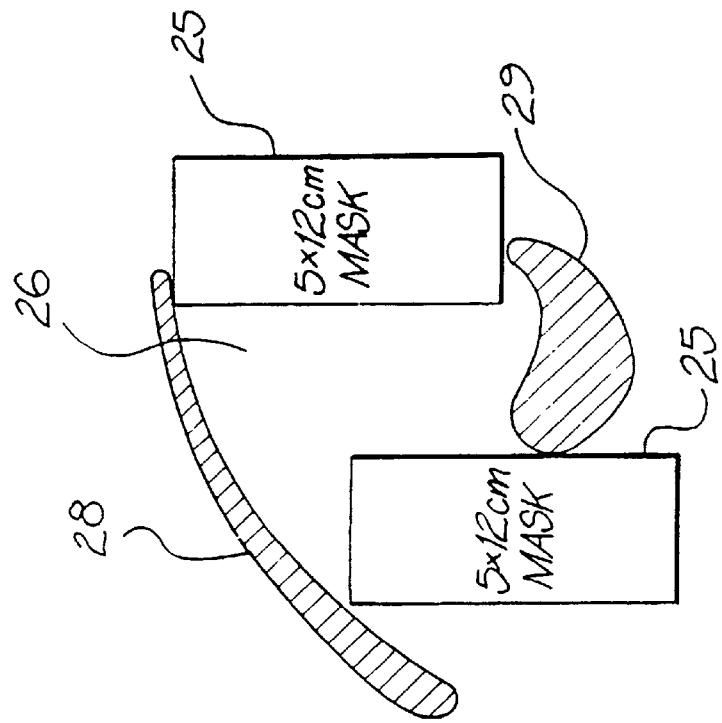
FIG. 6 is a schematic diagram, illustrating a process of analyzing an imaged hide in order to rank the hide.

Conventionally, the "quarter" method is used to rank leather. A template, for shoe products being 5×12 cm in area, is used to determine exactly what portions and how much of the total area of the particular leather sample can be used for shoe products. The template is matched with each portion of the leather. Any portion of leather including a defect falling within the template may not be useful. FIG. 6 shows a template 25 adjacent to a serious individual defect 28 and other defect 29. The area 26 is unlikely to be useful as wherever the template is placed within that area it will impinge upon a defect.

The processing means 17 further processes a stored contour map of a particular leather sample by passing a computer generated "template" across the map to determine cuttable areas of the leather sample. The template is first passed in parallel vertical passes across the entire surface of the map and then in parallel diagonal passes across the entire surface of the map 45° to the vertical and then further diagonal passes across the map at 135° from the vertical (i.e. two diagonal lines which intersect each other at 90°). The diagonal passes may be made in the range ±45°. Information on the total cuttable area is provided and also on the absolute area of the defects of any particular leather sample. This information can also be provided to the leather manufacturer.

The leather processor is thus provided with detailed information following an objective analysis of a particular leather sample to determine its usefulness in manufacturing leather products. Further, an objective ranking and pricing of any particular leather hide can be obtained using this system.

In this particular embodiment, a Line Scan Dalsa Camera was used. The light source utilized a double acrylic lens to focus a strip of illumination on the sample. One fiber optic guided light source powered by a variable DC power supply was used as the illumination source. An IPX Sun SPARC Station Coupling with the Imaging Technology series 150-40 boards, together with a Convolver-Arithmetic Logic Software Library was applied to process image data.

One problem of the visual inspection system embodiment of FIGS. 1 and 2 is that in order to pass the material sample 2 over the former roller 2 and between the tensioning rollers 8 and 10, some manual handling of the sample 2 is required. In a work place situation, this can be a safety hazard. The operator's hands could get caught in either set of rollers 8, 10 or 7, 9 and cause serious injury. Another disadvantage is that the material sample 2 is unsupported between the former roller 4 and each of the sets of rollers 8, 10 and 7, 9. This could result in "runaway" of the material sample i.e., the sample may be misfed in the wrong paths between the rollers.

Yet a further problem with this embodiment is that tensioning is applied in only a single direction, from left to right in FIG. 1 over the former roller 4. Although defects and scars will be made more visible by the applied tension in that direction, defects and scars which run in other directions on the hide sample may not be made sufficiently visible for sufficiently accurate detection or examination.

FIGS. 7 through 13 are various schematic views of a second embodiment of a visual inspection system in accordance with the present invention.

Figure 8:
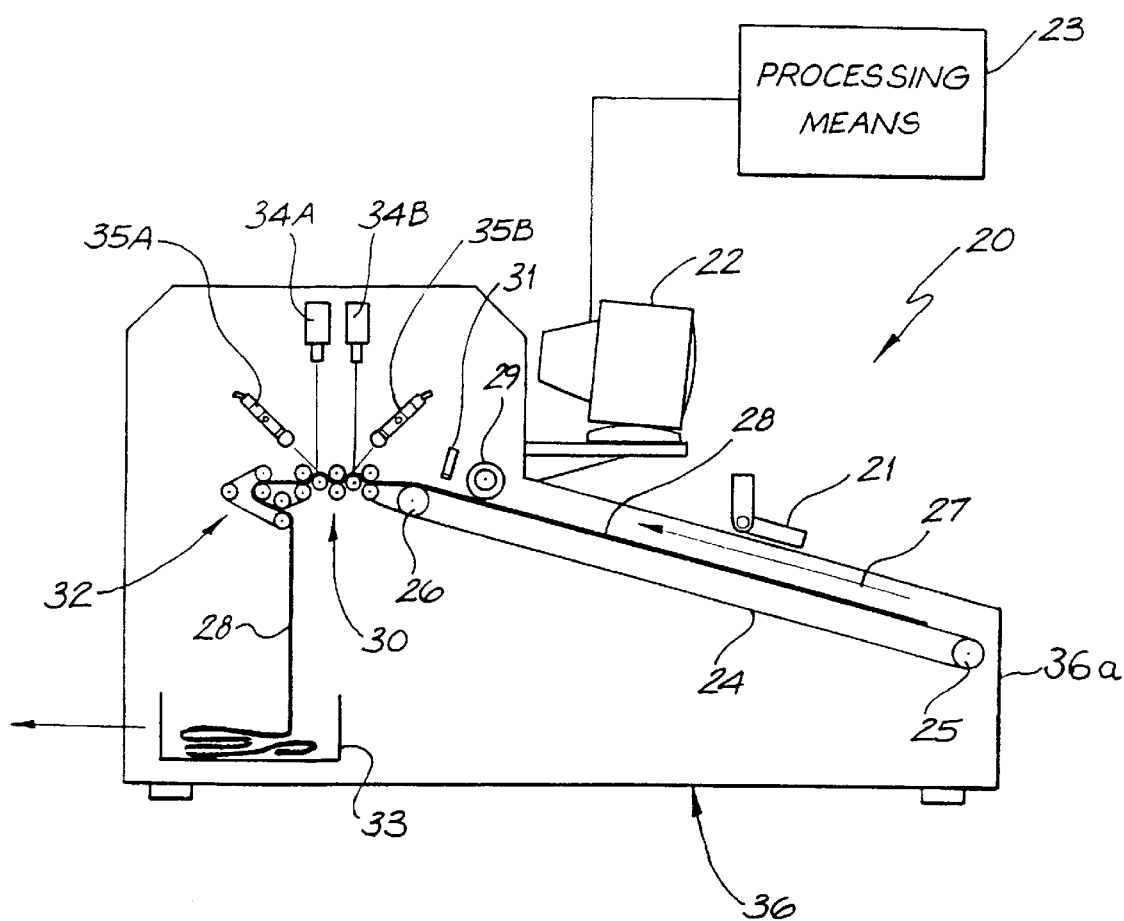
FIG. 8 is a schematic fill side view of the second embodiment of the visual inspection system.

Referring to FIG. 8, reference numeral 20 designates generally a handling and processing system for non-rigid materials, such as leather hides. The arrangement comprises an operator panel 21, a monitor 22 to enable images of the material to be viewed as the imaging process is ongoing and a processing means 23 for processing image information to identify defects, determine their position and make an examination of them so that they can be classified.

The system further comprises an infeed conveyor belt 24 driven by conveyor rollers 25 and 26 in the direction indicated by arrow 27. A non-rigid material sample 28 is passed along the conveyor 24 into a tensioning, support and imaging section 30. Tensioning, support and imaging section 30 is described in more detail later on with reference to some of the other Figures. A cleaning roller 29 is provided and is positioned to contact the sample 28 prior to the samples entry to the tensioning, support and imaging section 30. A color sensor 31 is positioned after the cleaning roller 29 to detect a color of the sample 28.

An outlay section 32 is provided for feeding the sample 28 from the tensioning, support and imaging section 30 into a bin 33, for subsequent collection. The outlay section 32 comprises a plurality of rollers, which extend width ways the same length as the rollers (to be described later) of the tensioning, support and imaging section 30. Imaging means, comprising CCD's 34a and 34b are provided for imaging areas of the sample 28. Light sources 35a, 35b are provided for illuminating the area to be imaged.

The entire arrangement is supported by a frame 36. Drive motors, $M_3$, $M_4$, $M_5$, $M_6$ are schematically illustrate in FIG. 13 for the tensioning, support and imaging section 30 rollers and for rotating the formers (see later). The frame 36 comprises two side portions 36a, 36b (see FIG. 13) only one of which is shown in FIG. 8. The side portions 36a, 36b mount bearings for supporting the rollers of the arrangement.

A more detailed description will now be given of the imaging means and the tensioning, support and imaging section 3C, with reference in particular to FIGS. 7 through 13.

The tensioning, support and imaging section 30 comprises three sets of rollers. Set 1 comprises rollers 40a and 40b. These are feeding rollers for feeding a sample 28 (not shown) into an imaging area. Rollers 40a and 40b support a pair of feed belts 41 and 42 which are moved in the directions indicated by the arrows A, B, C, D, following rotation of the rollers 40a and 40b as indicated by arrows E and F. Note that belt 41 is formed as an end portion of infeed conveyor 24. Belt 42, however, is not shown on FIG. 8, for the purposes of clarity. It will be appreciated that a further roller or mounting is required to support the end of the belt 42 opposite from the roller 40b. This further mounting is not shown, again for purposes of clarity. Belt 41 may not be the same belt as belt 24, but may be a separate belt.

In operation, the material sample is fed in at 43 between the rollers 40a and 40b and between the belts 41 and 42. As it is fed in, therefore, it is enclosed and supported by belts 41 and 42, which assist in keeping the material sample as flat as possible and avoids the need for an operator to feed the sample into the rollers 40a, 40b.

Once through the feed rollers 40a, 40b, the material sample is passed over a first former or inspection roller 44. While passing over the first former, the material sample is still maintained supported between upper and lower belt sets, which will be described in more detail later. Substantially flat upper surface portions 45 of the former 44 provide imaging areas for imaging of the material sample. A second set of rollers comprise tensioning rollers 46, 47. These rollers are arranged to be driven in the direction indicated by arrows G and H, and in operation the sample passes between them, entering at 48. As it passes between the rollers, the sample is maintained and supported between upper and lower belt sets, as will be described in detail later. Roller 46 and 47 are driven slightly faster than rollers 40a and 40b in order to tension the sample as it passes over former 44, the tension being applied in the direction from left to right, perpendicular to a longitudinal axis 49 of the former 44. As with the first embodiment above, the value of the tension applied will depend upon the thickness and type of leather and size of hide and calibration should be made with different types and thicknesses of leather to assess the optimum tensions to be applied for each type/thickness. Tensions will generally be in the order of 0.2 to 2.0 newtons/mm.

Figure 7:
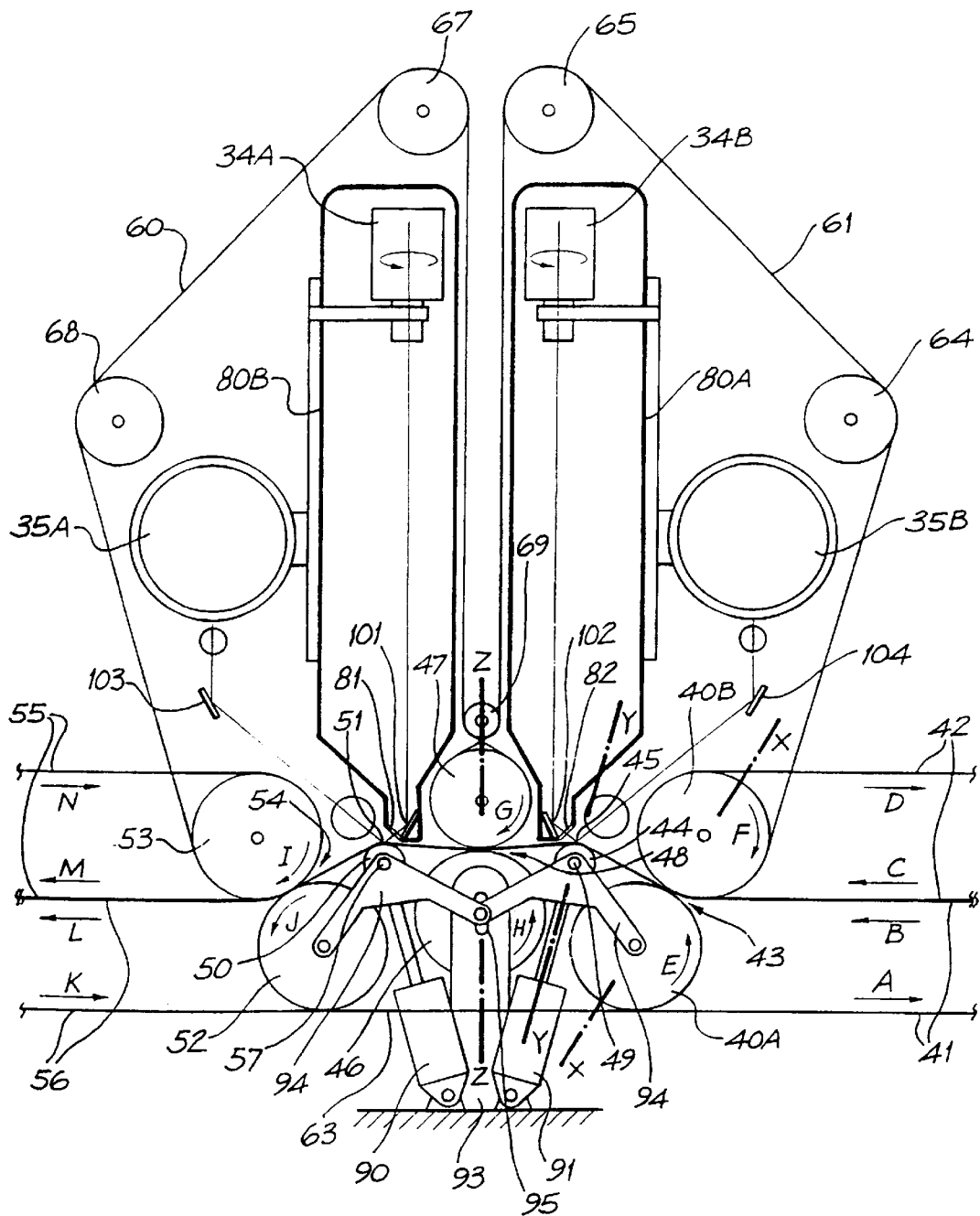
FIG. 7 is a side view of a portion of a visual inspection system in accordance with a second embodiment of the present invention.

A second former or inspection roller 50 is provided displaced from the first former 44, to the left of it in the drawing of FIG. 7. In operation, the material sample is also passed over this former, which, includes a plurality of top surface portions 51 which are substantially flat and which provide further imaging areas for supporting the sample while it is imaged. As the sample is passed over the further former 50, it is supported between upper and lower belt, sets, as will be described in more detail later.

A third set of rollers 52, 53 is provided, to the left of the further former 50 in FIG. 7. In operation, the material sample is passed between the rollers 52, 53, entering at 54, as the rollers are driven to rotate in the directions indicated by arrows I, J. After passing between the rollers 52 and 53 the material sample is conveyed away from the tensioning, support and imaging section 30, by belts 55 and 56, which travel in the directions indicated by K, L, M and N. Again, as the material is conveyed away from the tensioning, support and imaging section 30, it is fully supported between the belts 55 and 56. The material sample is thus fully supported over the entire length of its traverse into, through and away from the tensioning, support and imaging section, 30. No operator intervention is therefore necessary for feeding of the material through this area and danger to an operator is therefore minimized.

Rollers 52 and 53 are arranged to be driven at an incremental speed greater than rollers 46 and 47, to thus apply tension to the material as it is passed over the further former 50, in a direction perpendicular to a longitudinal axis 56 of the further former 50.

The arrangement of the belt sets for feeding the material through the tensioning, support and imaging section 30, will now be described with reference to the Figures, and with particular reference to FIGS. 12A, 12B and 13. The same reference numerals are used throughout to designate the same components.

Figure 12A:
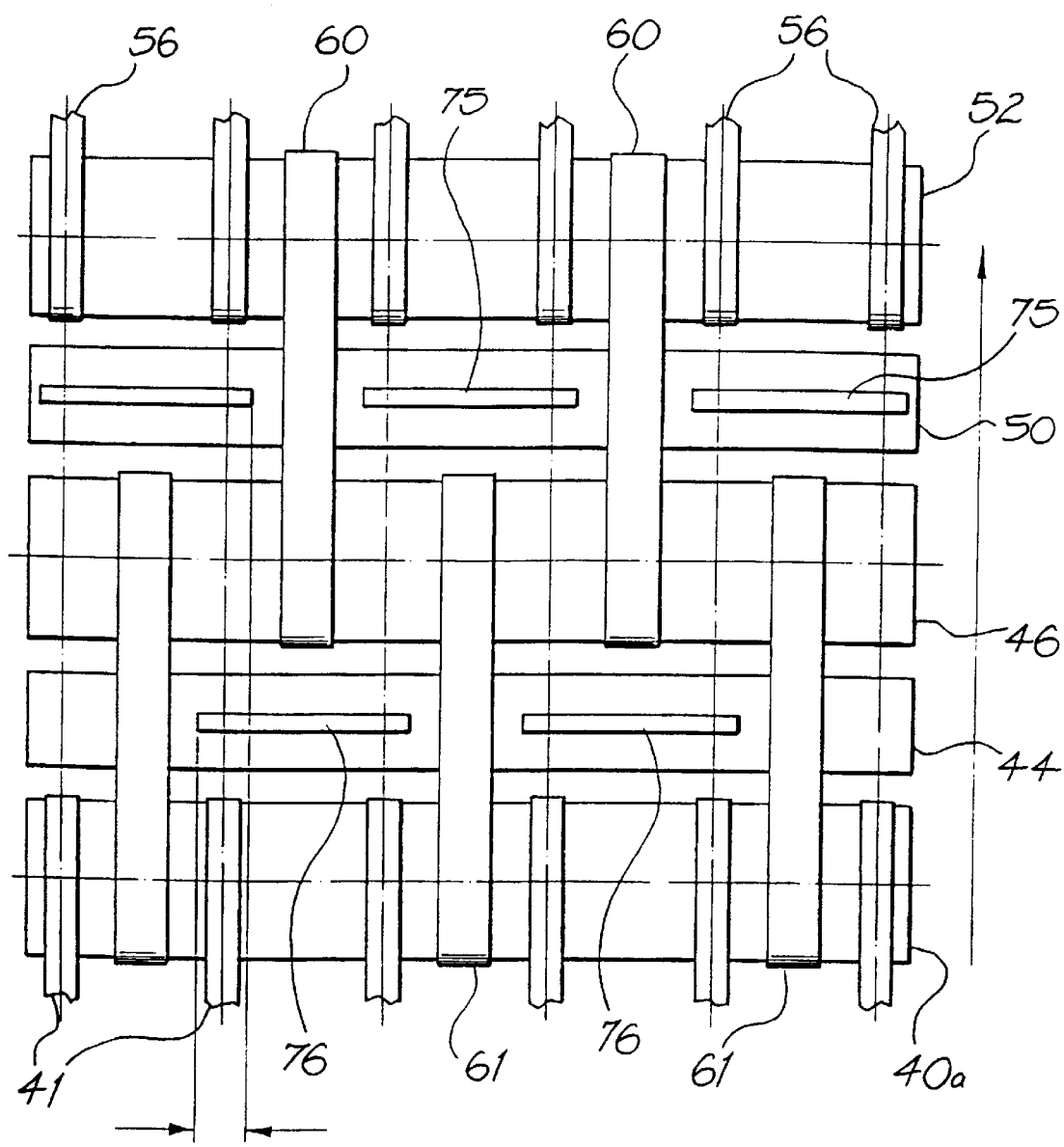
FIG. 12A is a schematic view of a portion of the visual inspection system of the second embodiment, illustrating imaging and tensioning areas and a top support belt arrangement.
Figure 12B:
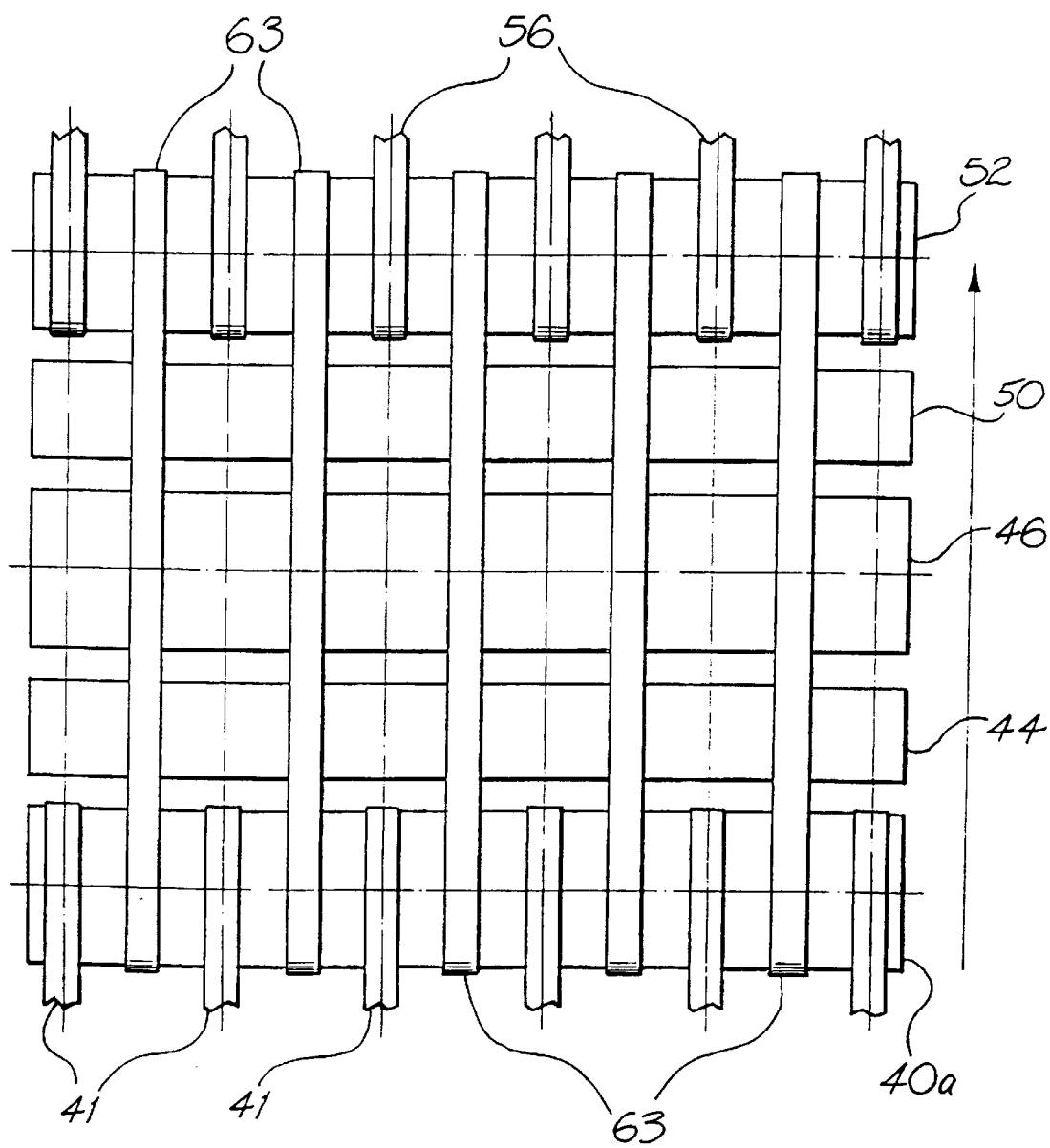
FIG. 12B is a further view of the portion of FIG. 12A, but this time illustrating the paths of bottom support belts.
Figure 13:
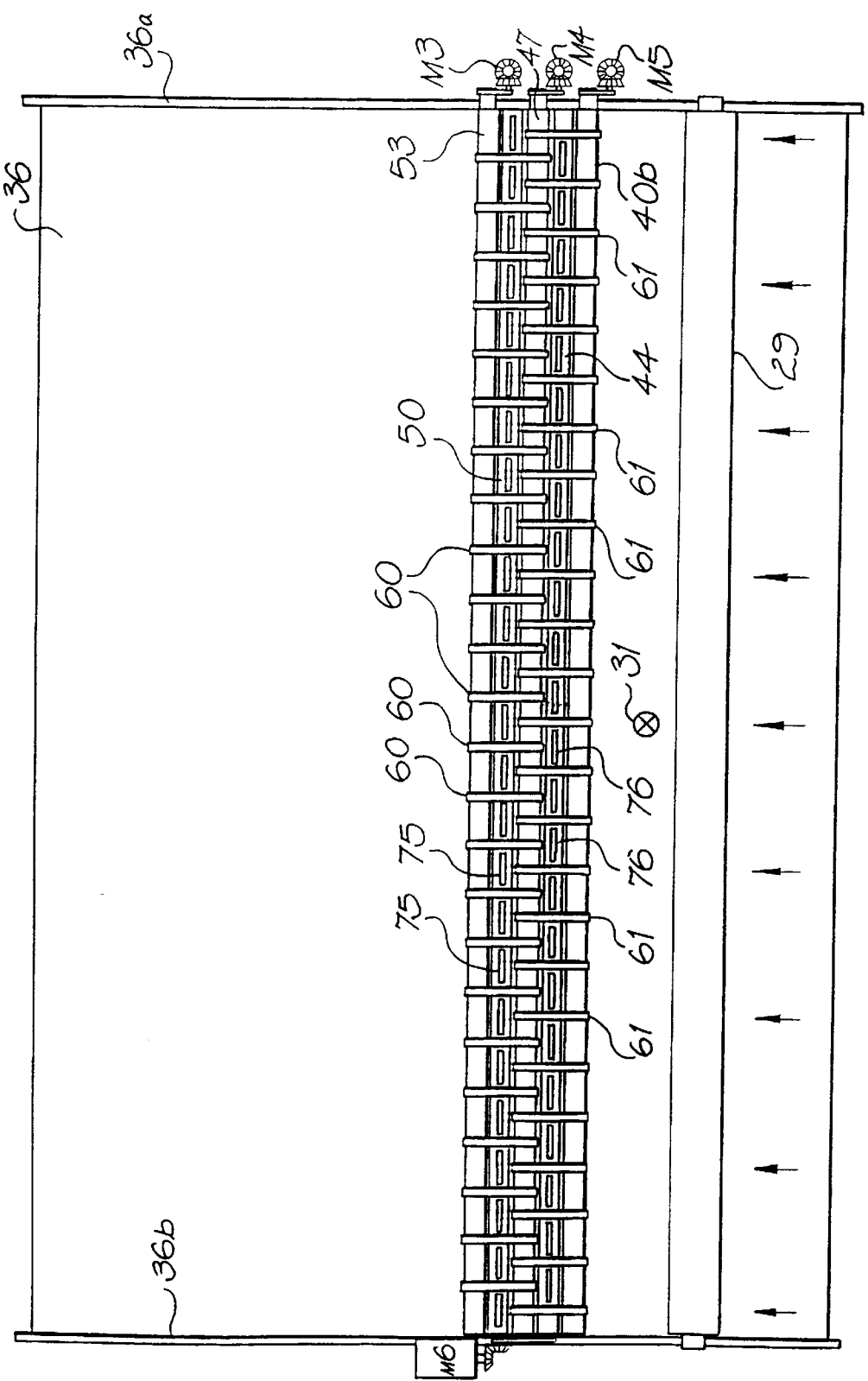
FIG. 13 is a further partial top view of the second embodiment of the visual inspection system.

FIGS. 12A and 12B are top views of the bottom rollers of the tensioning, support and imaging section 30 and the formers 44 and 50, being a view of only a portion thereof, in plan, illustrating positions of the belt sets involved., in order to assist with the explanation of the arrangement of the belt sets. For clarity, FIG. 12A illustrates top belt sets, but not bottom belt sets and FIG. 12B illustrates a bottom belt set but not top belt sets.

Throughout the material samples traverse of the tensioning, support and imaging section, it is supported between upper and lower belts. The top belts comprise a rear top belt set 60 and a front top belt set 61, All belts which are associated with any of the three roller sets described in relation to FIG. 7 comprise a plurality of webbing elements which are interleaved, so that they can move relative to each other. A belt comprised of a single integral webbing would prevent motion of the arrangement. The top belt sets, bottom belt set and the belts 56, 55 and 41, 42, comprise a plurality of separated webbing elements. For example, front top belt sets 61 comprises 25 separate webbing elements, as best illustrated in FIG. 13. Note that any number of webbing elements may be provided, depending upon the length of the rollers and required separation between the webbing elements.

As well as the belts 56, 155, 41, 42, illustrated in FIG. 7, the arrangement also comprises a front top belt set 61 and a rear top belt 60 (FIG. 12A), and a further bottom belt set 63 (FIG. 12B). The bottom belt set 63 passes around rollers 40a, 46 and 52 and over formers 44 and 50. All webbing elements of the belts are interleaved to enable motion of the belts, as will be appreciated by the skilled person. Rollers 64, 65, 67, 68, 69 are illustrated in FIG. 7 for carrying the top belts 61, 60.

In operation, as the material sample enters tensioning, the support and imaging sections 30, between rollers 40a and 40b, it is contacted by the front top belt set 61 and the leading edge of the bottom belt 60. The material is thus maintained supported between the front top belt set 61 and the bottom belt 63 as it passes over the first former 44. The rear top belt set 60 is contacted at roller 46, so that at that roller both the rear and front belt sets, and the lower belt are still in contact with the material. At further former 50, the material is still in contact with the rear top belt set 60 and the bottom belt set 63. As it leaves the tensioning, support and imaging section 30, the material is supported by belts 55 and 56. The material sample is thus totally supported throughout its traverse of the tensioning, support and imaging section 30.

Figure 9:
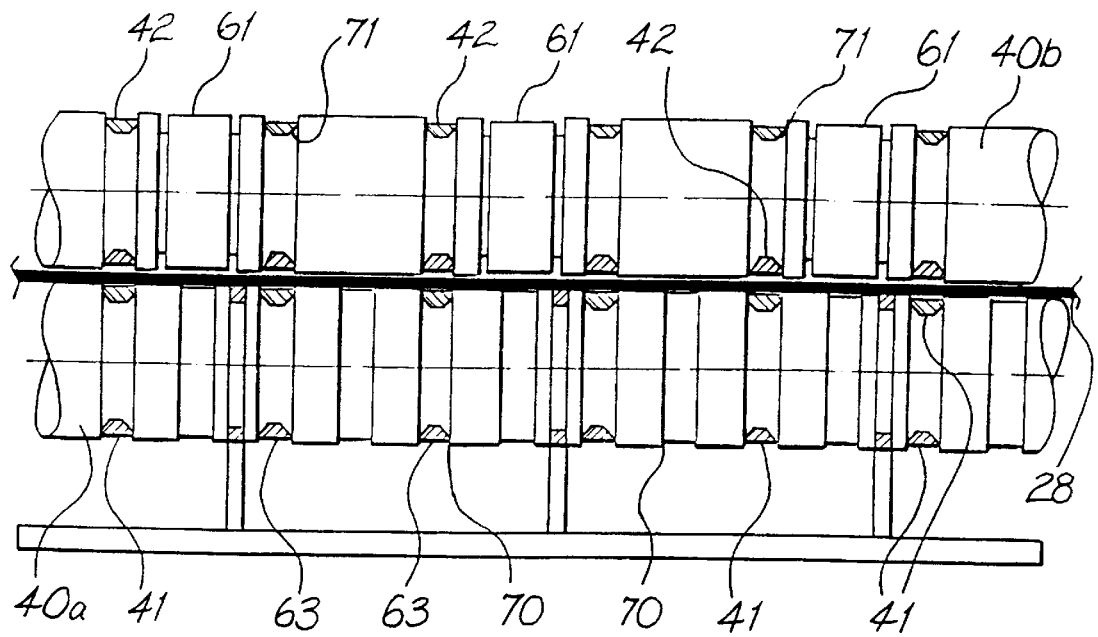
FIG. 9 is a partial section on line XX of FIG. 7.
Figure 10:
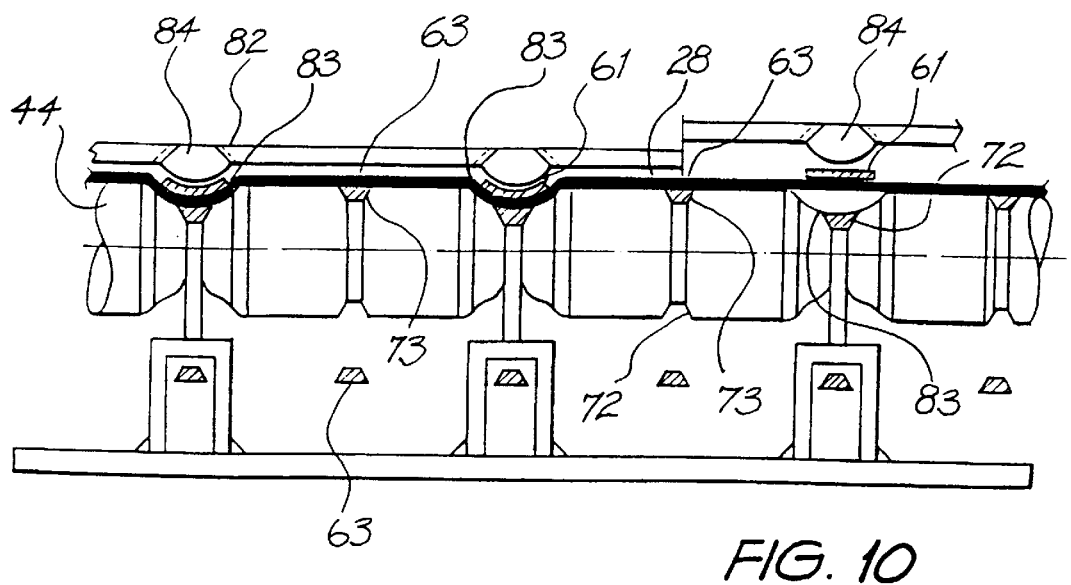
FIG. 10 is a partial section on line YY of FIG. 7.
Figure 10A:
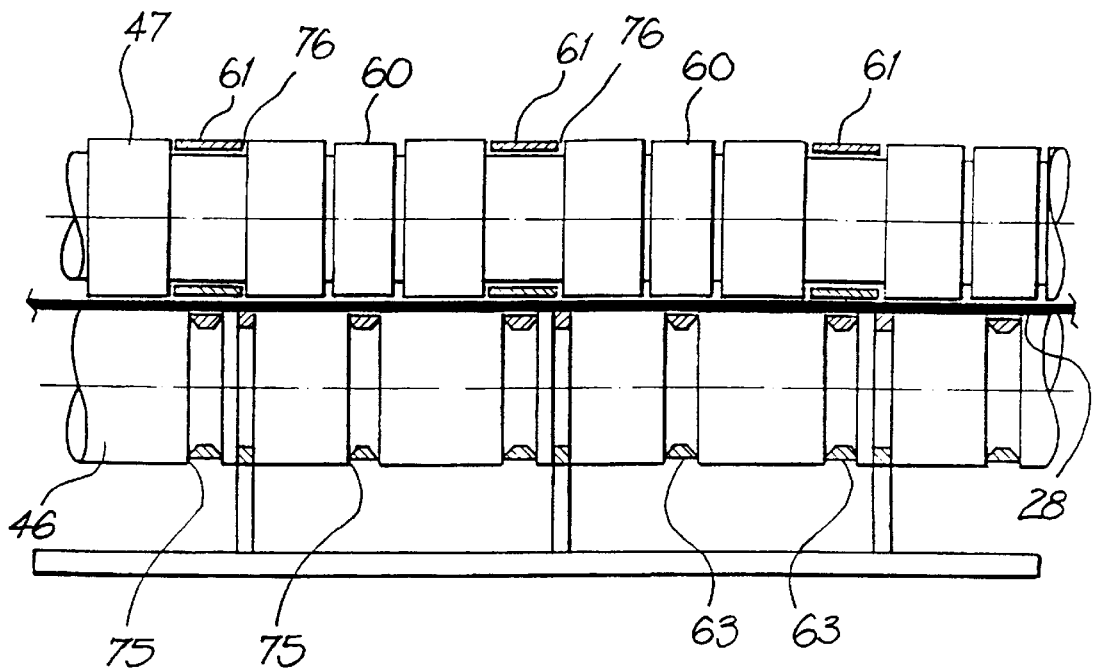
FIG. 10A is a partial section on line Z—z of FIG. 7.

As is clear from FIGS. 9, 10 and 10A, the belt webbing elements are arranged to run through slots 70, 71, 72, 73, 74 75, 76 in the respective rollers.

One problem with the belt arrangement of this embodiment, is that because the material sample is always sandwiched between two belt sets, it is not possible to obtain a single image of a full width of the material at any one point in the traverse through the tensioning/support and imaging section.

To overcome this problem, the sample is imaged at two separate areas through the traverse, the first area being provided by top surfaces 45 on the first former 44 and the second area being provided by top surfaces 51 of the further former 50. A plurality of imaging windows 75, 76 are defined for the imaging areas. This is most clearly shown in FIGS. 12 and 13. It can be seen that the windows 75, 76 are staggered with respect to each other. The portion of the material which did not get imaged as it passed over the first former 44, therefore, will get imaged as it passes over the further former 50, through imaging windows 75. The processing means 23 then operates, when it is building up the image of the material sample, to interleave together the staggered views of the image. Two CCD's, 34a, 34b are provided to image the two imaging areas.

The roller sets 46, 47 and 52, 53 tension the material sample in a direction transverse to the longitudinal axes 49 and 56 of the formers 44 and 50 Where the material is leather hide and is fed through the section 30 in a direction transverse to the direction of the beasts backbone in its lifetime, this tensioning direction will open the majority of defects on the hide for imaging. It will not affect to as great a degree scars and defects which extend in other directions, and particularly will not substantially affect scars and defects which extend in the same direction as this tensioning direction. To address this problem, means are also provided in this embodiment to tension the material in a direction which is substantially at right angles to the tensioning direction provided by the roller arrangements 47, 46, 52, 53.

Figure 11:
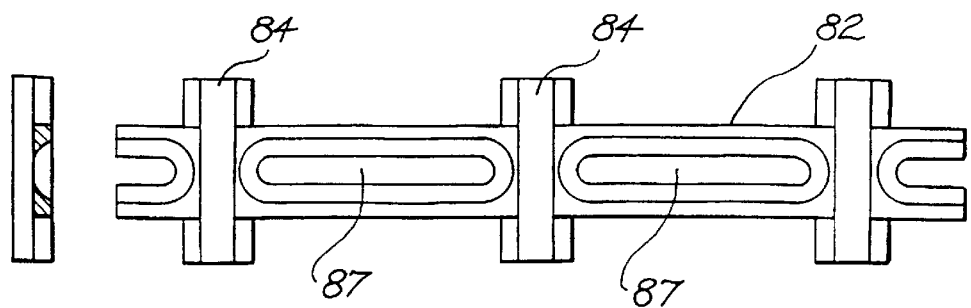
FIG. 11 is a top view of a lateral tension bar element of the second embodiment.

Frames 80A, 80B support first 81 and second 82 lateral tension bars. FIG. 11 shows a bottom view of a portion of lateral tension bar 82.

As well as the sections 51 and 45 of each former which provide surfaces for supporting the material in imaging areas, there are also provided a plurality of depressions, as shown in FIG. 10, reference numeral 83. As best shown in FIG. 10, lateral tension bar 82 comprises a plurality of convex projections 84 which are positioned and arranged to be able to fit into the depressions 83 in the former 56. The lateral tension bar 81 and former 44 have a similar arrangement.

The frame 80 is mounted on mounts 85, 86 which can be raised and lowered to raise and lower the lateral tension bars 81, 82 away from and towards the respective formers 44, 50. In the lowered position (see FIG. 10) the projections 84 extend into the depressions 83 and force portions of the material sample 28 (FIG. 9) into the depressions 83. Note that the upper belt 60 is also forced into the depressions. This results in the application of tension to the portions of material 28 extending across the surfaces 51, the tension being in a direction substantially parallel to the longitudinal axis 56 of the former 50. A similar arrangement and operation applies to former 44 and tension bar 81, This applied "lateral" tension is able to increase the visibility of scars and defects which do not extend in the usual direction.

In FIG. 10 the tension bar B2 is shown in raised (right hand side of Figure) and lowered positions.

The tension bar 82 (the same arrangement applies to tension bar 81) has a plurality of slots 87 which extend through the bar 82 and are coincident with imaging windows 76.

The CCD'S 34a and 34b are mounted to the frames 80A, 80B so that they are raised and lowered with the bars 81, 82, in order to maintain a consistent distance between the bars (which rest on the surface of the material sample) and the CCD's 34a, 34b, in order to maintain focus.

Materials such as leather hide may vary quite significantly in thickness, even over the extent of a single material sample. This creates a problem for an imaging means which must focus precisely on the surface of an area being imaged. If the surface profile is changing, the height of the area to be focused on relative to the imaging device will continually change. This embodiment of the invention addresses this problem.

Referring to FIG. 7, formers 50 and 44 are resiliently mounted on mounts 90, 91, respectively. The arrangement is such that the formers 50 and 49 can move upwards or downwards, although they are urged in an upward direction. The tension bar, however, in operation prevents the formers 44, 50 from moving upwards. Where the material of the sample increases in thickness, therefore, formers 49, 50 are forced downwards. The top surface of the material, however, maintains its distance from the CCD's 34a, 34b, as dictated by the tension bars 81, 82. The linkage arrangement 94 connects the rollers 46, 40a, 52 with the formers 49 and 50.

A slot 95 in central mounts 93 allows vertical motion of the linkage arrangement 94.

Pivotable mirrors 100, 101, 102, 103 are provided to adjust the position of the imaging area for both formers 49 and 50. Sensitivity of adjustment is increased by the positioning of mirrors 101 and 102 relatively close to the formers 49 and 50. Light sources 35A, 35B provide a source of light, incident on mirrors 103, 104.

As with the embodiment of FIGS. 1 and 2, it is important that the background color of the support (the former) in the imaging area provides sufficient contrast to the color of the material sample to enable the imaging and processing system to detect the borders of the sample. In this embodiment, each of the four sides of each of the formers 44 and 50, is of a different color. The color sensor detects the color of the hide as it approaches the support, tension and imaging section 30, and control means operates a motor to rotate the formers 44 and 50 to present as an imaging surface the surface of the color which provides the most contrast.

Note that this device is not intended to be used with "raw" hide, which has not been colored. Raw hide would have a number of markings and blemishes on it which would not be defects, but merely variations in color of the hide. The system is intended to be used with hide which has undergone some preliminary treatment steps, in particular with hide that has been dyed or at least with hide which is at the "wet blue" stage.

An alternative method of detecting and verifying defects in the hide will now be described with reference to FIGS. 14 through 17. Rather than breaking the hide image down to discrete areas of $10^4$ pixels, this alternative embodiment examines the area of the hide to determine and verify "edges" of defects. Some work has been done on statistical analysis of edges in images, but the present invention adds to it significantly in order to provide for accurate detection and verification of defects.

The input for the system of this embodiment is the digital image of a leather hide, the output is a defect map which carries the location and severity of each defect.

Scars and mites usually create intrusions and extrusions on a leather surface. These intrusions and extrusions on the surface form "hills" and "valleys" of different height and depth. Consequently, these hills and valleys create small patches that have various reflecting angles with respect to light sources and camera, and appear darker and/or brighter than the otherwise homogeneous region.

A leather surface usually is a surface with certain textures. The defects can vary in many ways, such as the severity which affects the composition of grey level values in the area of consideration, the area and shape of the defect, etc., as mentioned above.

The texture in a hide can vary in many ways too. The degree and type of texture can vary from region to region in the same hide. These are the physical characteristics of the texture itself. Same level and type of texture can also appear differently in an image because of the external conditions that are affected by illumination, local thickness variation, reflective angle, surface finish etc.

Surface finish is a very important factor. High reflective surface such as high shine leather hides are much more difficult to analyze because they are easily affected by the external factors (such as illumination, etc). Dark color adds difficulty to the problem, because with a dark color, the light intensity of the light source needs to be strong and it makes the high reflective surface behave more unpredictably.

Because of these facts, a defect may not appear to be a defect in a region that is heavily textured or having heavy noise. Or a severe defect may appear to be less serious in some region. Also, natural hide texture or noise can be falsely detect as defects due to the same reason. Therefore, misdetection and false detection happen often.

Due to the size of the hide (2×3 square meters), there are basically two problems:

1. the same type of defects appear differently in different regions of the hide;
2. the amount of information to be processed is large. (about 50–70 MB/hide).

In this embodiment we examine the defects by examining the boundaries or edges of the defects. Edges in a grey level image are discontinuities in image intensity profiles. Usually, an edge can be regarded as the boundary between two regions with relatively distinct grey level properties. Edges may represent boundaries of objects, marks, shadows and shading.

Figure 14:
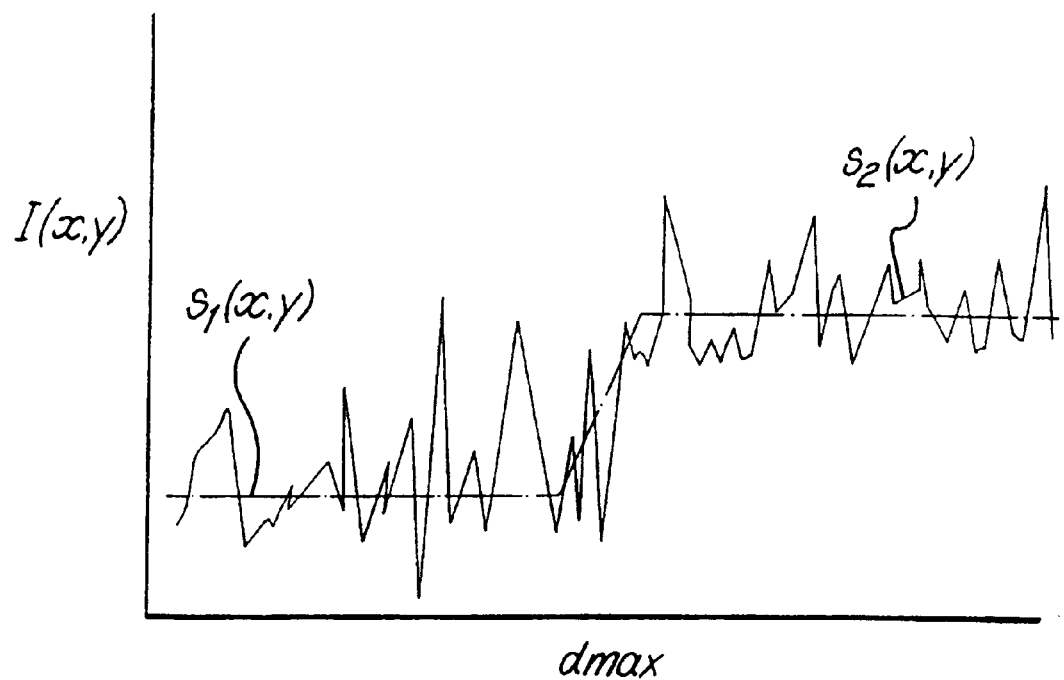
FIG. 14 is a graphical representation of a "noisy edge" of a defect in a material sample, for illustrating an alternative method of identifying defects.

The edge model we consider is shown in FIG. 14. This model is a generalized edge which consists of a step edge and noise and/or textures. The cross-sections of the edge are taken in the direction of $d_{max}$, for which the slope measured is maximum (note that x,y are the coordinates of the particular point on the image).

To examine an edge, and determine if a candidate edge is really resulted from the defect that is surrounded by it, we need to consider the following:
  the definition and characteristics of defect;
  the definition and characteristics of normal surface,
  the external conditions such as illumination, local thickness variation, reflective angle, surface finish and textures.

Normally, some of the above considerations are taken into account in the process of generating edges. However, we propose the idea of defect examination by examining their edges and this work is the first on examining candidate edges by considering these situations. The benefits of using this method can be surmised as:
  saving computational time considerably, thus making this method more suitable for real industrial inspection tasks in production environment;
  providing more accurate description of the characteristics for both normal region and defects that are separated by the edges being examined, thus making accurate decision-making possible;
  giving accurate information on both the position and the severity of a defect;
  making it easier to adapt this method for other applications (not only leather surface inspection).

Intensity changes in a grey level image take place at many spatial scales. t is realized that fine intensity changes are detected by small scale operator and coarse intensity change information is collected by large scale operator. Edges in the original image that can be detected at small scales may disappear at coarser scales, and spurious edges can occur at a coarse scale. In order to detect edges occurring at a variety of spatial scales, multi-scale edge detection method has been used. Intensity changes at different scales can be obtained by applying edge operators of different sizes. The final results are obtained by combining the edge information recovered at each scale. This is how edge detection is normally applied. This method is computationally expensive, because of the following reasons:

smooth operation which is usually the most time consuming operation needs to be applied on to an image more than once; each scale operator has to be applied once, for instance, if operations of scales need to be applied, we will have to do n such operations; and the greater the value of a, more time consuming the computation becomes;

combining of edge information obtained at each scale is highly complex.

At the same time, undesirable intensity changes due to noise and/or natural textures may also be picked up in either small or large scales.

It has also been suggested that an image he segmented into regions that have relatively homogeneous intensity changes, and then edge operators are applied to the regions accordingly with proper scale parameters. However, part of the problem with this method is also its large computation demand. Gaussian smoothing can be done separately in rows and columns on the whole image if it is to be smoothed with a single scale, thus the computation can be reduced. The separability of Gaussian can reduce a 2D convolution into a pair of two, successive 1D convolutions. Therefore, a computation complexity of $O(M^2)$ is reduced to $O(M)$. However, if the whole image is divided into regions of different scales, this timesaving characteristic cannot be exploited efficiently. Also, if an image is smoothed with different scales in different regions, there is discontinuity between the edges thus detected. If the smoothing kernel is large, the accuracy of the edge location suffers.

The method developed for the present invention uses the relatively time-consuming Gaussian smoothing operation to generate candidate edges of defects. Then the candidate edges are examined with a two-stage method.

The first stage of the method of the present invention includes the examination of each individual point (pixel) on an edge, determines whether or not that point (pixel) should be included on that particular edge. The examination scheme includes the comparison of three entities: the point a being examined (FIG. 15) an inner area that immediately surrounds the point and an outer area that is outside of the inner area. We consider the statistics of these three entities and have worked out the relationship between the given definition of defect and the statistics of these three entities. Then decision can be easily made.

Figure 15:
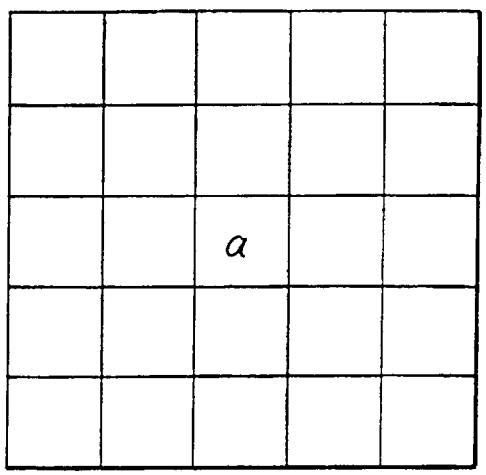
FIG. 15 is a graphical illustration of a point or pixel examination for determining the position of a defect.

The second stage is the consideration of an entire edge as a single entity as shown in FIG. 15, and then examines whether or not this edge is caused by noise or texture or real defect and then makes the decision of keeping it or removing it. The examination scheme is similar to the examination of an edge point described above. We still consider three entities. Here, we consider the entire edge as a single entity instead of a point on the edge. The length of the edge is also taken into consideration in this scheme. Since the areas we use are the areas next to the edge and have constant distant to the edge, the statistics from them give more accurate description of the edge and its neighborhood. Also, the relationship between the given definition of defect and the statistics of these three entities is given, so that examination of defect is achieved.

Figure 17A:
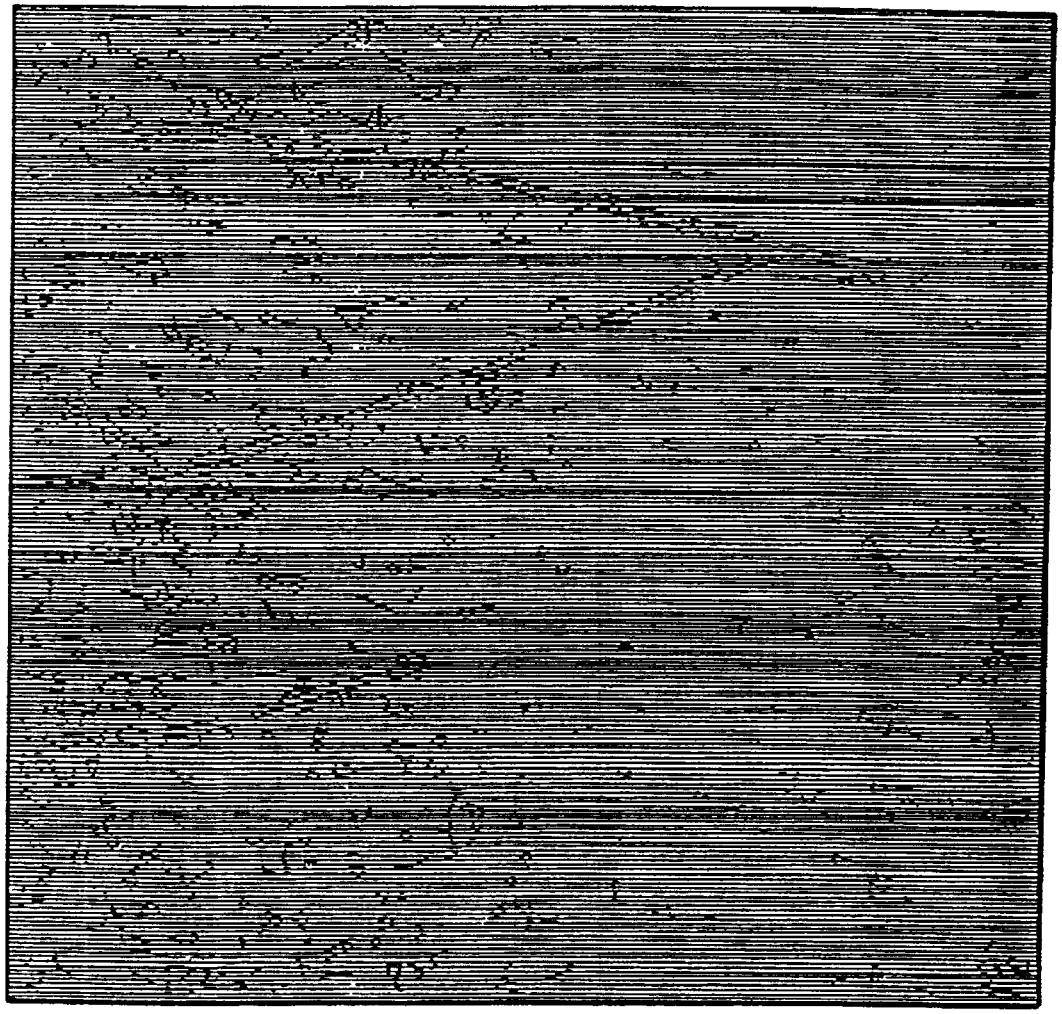
FIGS. 17A through 17C are example processed images of a leather hide surface showing, in turn, an original raw image (A), the image after edge detection has been applied in accordance with an embodiment of the present invention (B) and the image after an edge verification algorithm has been applied in accordance with an embodiment of the present invention (C).
Figure 17B:
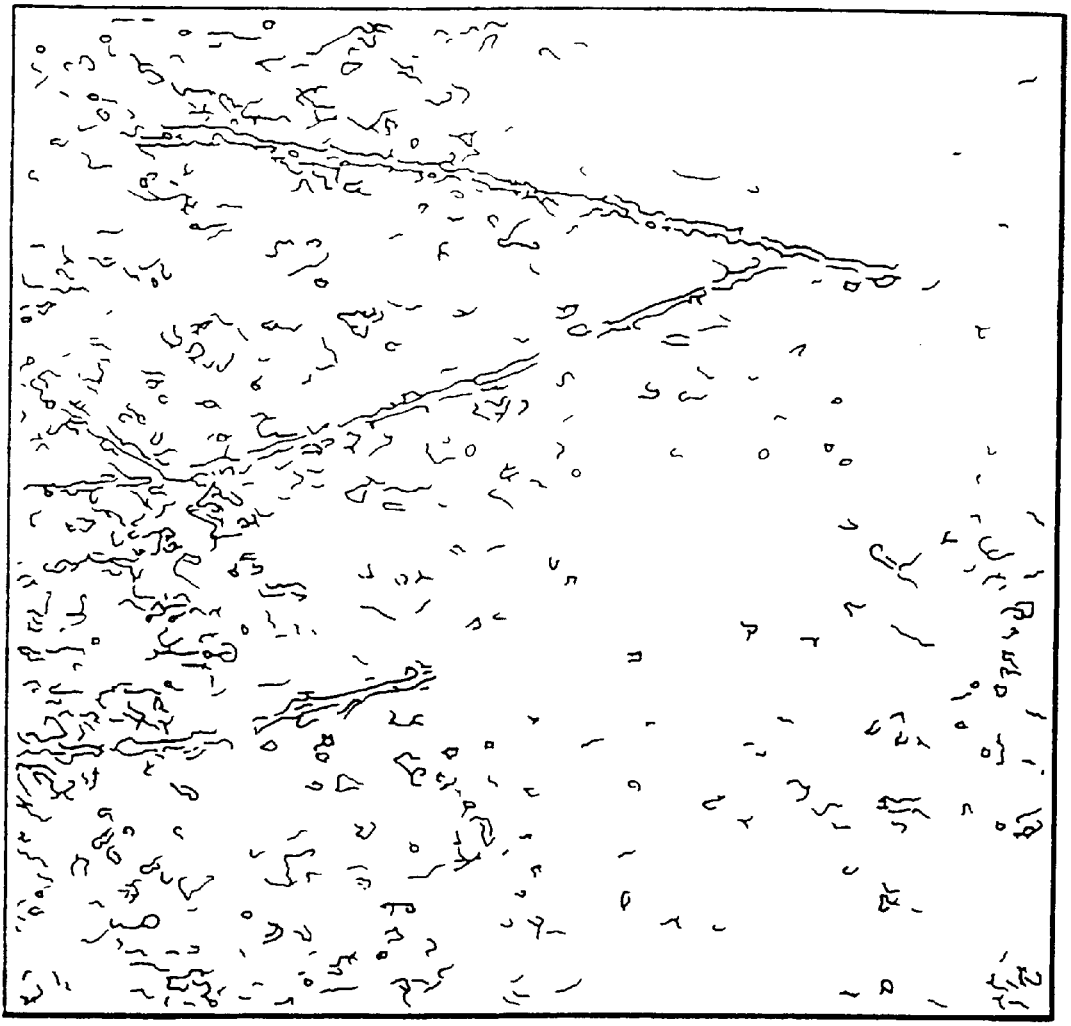
Figure 17C:
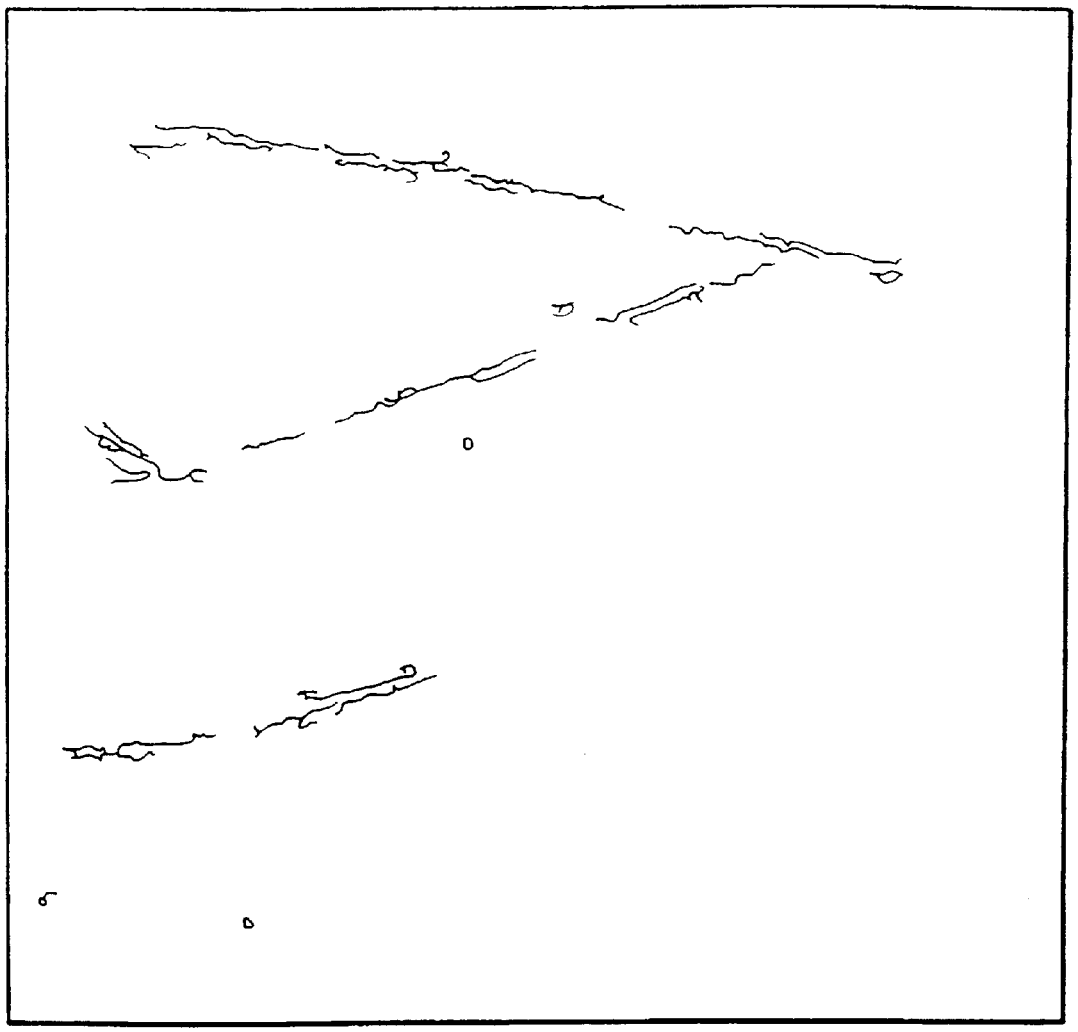

An example of defect examination is shown in FIG. 17.

Verification algorithm applied to a leather surface image with a heavy texture background on the left and smooth texture background on the right. (a) original image, (b) edge detector applied with σ=1.5, (c) after examination algorithm applied to (b).

The following is a flow chart of the defect examination process applied in this embodiment, detailing the algorithms involved.

Flow chart of defect detection and examination.

1. Using Canny edge operator to detect the possible defect edges. (John Canny, "A Computational Approach to Edge Detection," *IEEE Transactions on Pattern Analysis and Machine Intelligence*, Vol. PAMI-8, No. 6, November 1986, pp 679–697.)The algorithm of this edge operator can be briefly described as the following:

(a) Smooth the image with a 2D Gaussian function. The mathematical form of a 2D Gaussian is:

$$G(x, y) = \frac{1}{2\pi\sigma^2} e^{-\frac{x^2 + y^2}{2\sigma^2}}$$

To smooth an image I(x,y), we can simply apply a mathematical convolution between these two:

$$G(x,)y*I(x,u)$$

The resultant image will be a smoothed one. We can control the degree of this smooth operation by choosing different σ's in the 2D Gaussian. Consequently, the size of the Gaussian mask changes. The size of a Gaussian mask is m×m is determined by the following equation:

$$m = (\text{integer})(3\times\sigma+0.5)\times 2)+1$$

For example, if σ=1.5, then it will be 11, which means we will apply a window of size 11×11 onto the image and smooth the image accordingly. Therefore, the "block" associated with each pixel has 11×11=121 pixels. In this applicator the value of C is a constant, which indicates that the size of "block" is a constant. This feature takes advantage the fact that Gaussian smoothing can be done separately in rows and columns on the whole image if it is to be smoothed with a single σ. The separability of Gaussian can reduce a 2D convolution into a pair of two, successive 1D convulsions. Therefore, a computation complexity of $O(M^2)$ is reduced to $O(M)$.

(b) The computation of first derivative is carried out on the smoothed image. The edges of candidate defects are then detected. (described by John Canny, "A Computational Approach to Edge Detection," *IEEE Transactions on Pattern Analysis and Machine Intelligence,* Vol. PAMI-8, No.6, November 1986, pp 679–697.)

2. First stage of edge examination by considering each edge pixel and its neighborhood (FIG. 15). Before using the hysteresis suggested in (John Canny, "A Comnutational Approach to Edge Detection," *IEEE Transactions on Pattern Analysis and Machine Intelligence,* Vol, PAMI-8, No. 6, November 1986, pp 679–697), we examine edge pixels. Normally, whether or not an edge pixel is significant (in our application, whether or not an edge pixel represents a pixel on the edge of a defect) is determined by examining only the strength of the edge point this pixel represents. This approach appears to have problems in dealing with images having textures and/or noise, because the nature textures are not defects that have to be identified. Nature textures can have edges that have high strengths similar to the defects. This step of examination is designed for edge point verification. To each edge point (pixel in the image), we consider a neighborhood (block) in the fashion that the pixel being considered is located in the middle of the block. For instance, if pixel a in FIG. 15 is being examined, and the neighborhood to be considered is w×w, in this case, w=5. If we denote the edge strength of point a is a real defect edge point if $$E_s > c \div \sqrt{2SZ\alpha} \quad (1)$$

otherwise, this point does not represent a defect edge point. S in the above expression (1) is the standard deviation of the grey levels of the pixels in the block. α can be chosen as 0.2, 0.2, 0.3, etc. and Zα can be found from standard normal distribution tables. c is a consant representing the given threshold which can me chosen according to the nature of leather hides.

Figure 16:
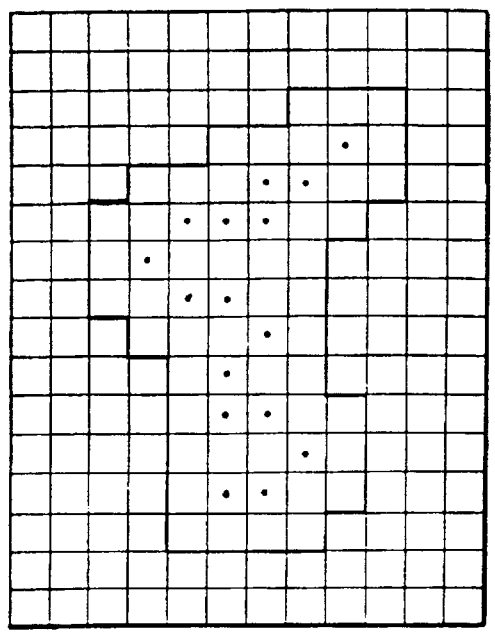
FIG. 16 is a graphical representation of an example defect "edge" for illustrating how a defect edge is determined.

3. Use of hysteresis method to generate edges by using only the pixels that have passed test (1)
4. Trace the contour of each edge thus detected.
5. Second stage of edge examination by verifying each individual edge as a whole entity. We need to generate an area that surrounds the edge and calculate the joint distribution. An example of the block that surrounds a candidate edge is shown in FIG. 16. We denote the edge strength of an edge as E. E is the average of the edge strength of each edge point on the edge, and can be calculated using.

$$E = \frac{1}{n}\sum_{f=1}^{2} E_S$$

where $E_S$ is the edge strength of the pixel on the edge. We have developed the following expression to test an edge to see whether it is defect edge or just an edge due to nature leather textures or noise.

$$E > c - Z\alpha \sqrt{\frac{1}{n}\left[\frac{2m-1}{m-2}Vxy - \frac{m}{2m-1}E_s^2\right]} \quad (2)$$

where $v_{XY}$ is the sample variance of grey levels of the pixels located in the block, 2m is the number of the pixels located in the block. The constants c and Zα and can be chosen in a similar way described for test (1).

If an edge with edge strength E passes the test (1) then this edge is an edge of defect and further process is required. Otherwise it is an edge of texture of noise, and it should be removed.

The system of the present invention may be useful other types of materials, not just leather.

Variations and/or modifications may be made in the invention as described in the specific embodiments without departing from the spirit or scope of the invention as described and defined in the following statements of claims.

What is claimed is:

1. A visual inspection system for non-rigid materials, comprising a mounting means for mounting a sample of the material, tensioning means for tensioning an area of the sample, an imaging means for obtaining an image of the area of the sample under tension, processing means for processing the image to provide information on any defects which may exist, drive and support means for supporting and moving the material sample relative to the imaging means whereby to tension and obtain images of a plurality of areas of the sample, wherein the tensioning means is arranged to apply tension to the area of the sample being imaged at any time in a first direction and in a second, different direction.

2. A visual inspection system in accordance with claim 1, comprising a former over which the material sample is tensioned to enable the imaging means to better perceive any defects in the material.

3. A visual inspection system in accordance with claim 2, the former being substantially elongate in shape and the tensioning means including means for applying tension in a direction substantially at right angles to a longitudinal axis of the former, whereby to tension the material sample over the former.

4. A visual inspection system in accordance with claim 3, wherein the tensioning means further comprises means for tensioning the material in a direction parallel with the longitudinal axis of the former.

5. A visual inspection system in accordance with claim 4, wherein a first surface of the former, over which the material sample is to pass, is formed by a plurality of at least partially convex or flat areas separated by depressions in the surface, and the tensioning means includes means for forcing portions of the material sample into the depressions as the material sample is passed over the former, whereby to tension the material sample over the convex or flat areas in a direction substantially parallel to the longitudinal axis of the former.

6. A visual inspection system in accordance with claim 2 wherein the former and imaging means are mounted for movement relative to each other, and compensation means are provided for automatically adjusting the relative positions of the former and imaging means in response to variations in thickness of the area of the material sample being tensioned, whereby to maintain a substantially fixed distance between the imaging means and the surface of the area of the sample being imaged.

7. A visual inspection system in accordance with claim 1, further comprising a light source for illuminating the area of the sample being imaged, the relative positions of the light source, imaging means and sample being arranged so that the imaging means perceives defect areas on the sample as having a different grey level than undefected areas.

8. A visual inspection system in accordance with claim 7, the light source providing a source of variable light intensity and incorporating focusing means for illuminating a strip of the sample.

9. A visual inspection system in accordance with claim 8, the light source being arranged to illuminate a strip of the sample.

10. A visual inspection system in accordance with claim 1, the drive and support means including a plurality of drive and support belts and wherein the arrangement of the plurality of belts is such that the material sample is supported throughout its movement relative to the imaging means.

11. A visual inspection system in accordance with claim 10, wherein a plurality of imaging windows are provided coincident with gaps in the belts the imaging means being arranged to obtain images of the areas of material sample passing by the imaging windows, whereby to obtain images of plurality of areas of the sample.

12. A visual inspection system in accordance with claim 1, wherein the second different direction is perpendicular to the first direction.

13. A visual inspection system in accordance with claim 1, wherein the imaging means comprises a charged coupled device (CCD) and a focusing means for focusing an image of the area being imaged onto the CCD.

14. A visual inspection system in accordance with claim 13, wherein the focussing means includes a pivotable mirror mounted close to the imaging area, whereby to result in increased focusing control.

15. A visual inspection system for non-rigid materials, comprising a mounting means for mounting a sample of the material, tensioning mean for tensioning at least an area of the sample, an imaging means for obtaining an image of the area of the sample under tension and processing means for processing the image to provide information on any defects which may exist, the processing means being arranged to statistically analyze gray levels of pixels imaged by the imaging device, by applying a normal distribution on either side of a medial gray level which is defined as undefected leather, and determining an extreme or extremes of the normal distribution as defining defected areas of leather.

16. A visual inspection system in accordance with claim 15, the processing means being arranged to produce a contour map showing the extent and location of defects in a material sample.

17. A visual inspection system in accordance with claim 16, the processing means further being arranged to scan the contour map with a template of predetermined area in order to determine the area of material which is useful for the manufacture of product.

18. A visual inspection system in accordance with claim 15, the processing means being arranged to analyze the image by analysing "cells" of the image separately, each cell forming a predetermined portion of the entire image.

19. A visual inspection system in accordance claim 15, the processing means being arranged to apply an edge detection algorithm to determine edges of defects in the material.

20. A visual inspection system in accordance with claim 19, the edge detection process comprising two stages, the first stage including an examination of each pixel in an edge and its surrounding area, and the second stage including an examination of the pixels on an edge and their surrounding area.

21. A visual inspection system for non-rigid materials, comprising a mounting means for mounting a sample of the material, tensioning means for tensioning at least an area of the sample, an imaging means for obtaining an image of the area of the sample under tension, processing means for processing the image to provide information on any defects which may exist, a former being substantially elongate in shape and defining a longitudinal axis, the former having a first surface, over which the material sample is to pass, formed by a plurality of at least partially convex or flat areas separated by depressions in the surface, and the tensioning means includes means for forcing portions of the sample material into the depressions as the material sample is passed over the former, whereby to tension the material sample over the convex or flat areas in a direction substantially parallel to the longitudinal axis of the former.

* * * * *